United States Patent
Kramer et al.

(10) Patent No.: US 11,155,524 B2
(45) Date of Patent: *Oct. 26, 2021

(54) AMINO ACID COMPOSITIONS

(71) Applicant: ThermoLife International, LLC, Phoenix, AZ (US)

(72) Inventors: Ronald Kramer, Phoenix, AZ (US); Alexandros Nikolaidis, Nea Killikratia (GR)

(73) Assignee: ThermoLife International, LLC, Chandler, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/893,319

(22) Filed: Jun. 4, 2020

(65) Prior Publication Data

US 2020/0297678 A1 Sep. 24, 2020

Related U.S. Application Data

(63) Continuation of application No. 16/746,348, filed on Jan. 17, 2020, which is a continuation of application No. 14/617,571, filed on Feb. 9, 2015, now Pat. No. 10,555,921, which is a continuation of application No. 13/920,081, filed on Jun. 17, 2013, now Pat. No. 8,952,046.

(51) Int. Cl.
| | |
|---|---|
| *C07D 233/64* | (2006.01) |
| *C07C 229/08* | (2006.01) |
| *C07C 229/24* | (2006.01) |
| *C07C 229/26* | (2006.01) |
| *C07C 237/06* | (2006.01) |
| *C07C 275/16* | (2006.01) |
| *C07C 323/58* | (2006.01) |
| *C07D 207/16* | (2006.01) |
| *A61K 31/198* | (2006.01) |
| *A61K 31/401* | (2006.01) |
| *A61K 31/4172* | (2006.01) |
| *A61K 33/00* | (2006.01) |
| *A61K 31/197* | (2006.01) |
| *C07C 279/02* | (2006.01) |

(52) U.S. Cl.
CPC .......... *C07D 233/64* (2013.01); *A61K 31/197* (2013.01); *A61K 31/198* (2013.01); *A61K 31/401* (2013.01); *A61K 31/4172* (2013.01); *A61K 33/00* (2013.01); *C07C 229/08* (2013.01); *C07C 229/24* (2013.01); *C07C 229/26* (2013.01); *C07C 237/06* (2013.01); *C07C 275/16* (2013.01); *C07C 279/02* (2013.01); *C07C 323/58* (2013.01); *C07D 207/16* (2013.01)

(58) Field of Classification Search
CPC .. A61K 31/197; A61K 31/198; A61K 31/401; A61K 31/4172; A61K 33/00; A61P 21/00; C07C 229/08; C07C 229/24; C07C 229/26; C07C 237/06; C07C 275/16; C07C 27/02; C07C 323/58; C07D 207/16; C07D 233/64
See application file for complete search history.

(56) References Cited

U.S. PATENT DOCUMENTS

| | | |
|---|---|---|
| 1,916,983 A | 7/1933 | Prince |
| 3,886,040 A | 5/1975 | Chibata et al. |
| 3,997,659 A | 12/1976 | Knohl et al. |
| 4,146,611 A | 3/1979 | Ondetti et al. |
| 4,379,177 A | 4/1983 | McCoy et al. |
| 4,743,614 A | 5/1988 | Terano et al. |
| 4,996,067 A | 2/1991 | Kobayashi et al. |
| 5,026,721 A | 6/1991 | Dudrick |
| 5,242,697 A | 9/1993 | Luca |
| 5,500,436 A | 3/1996 | Schonafinger et al. |
| 5,543,430 A | 8/1996 | Kaesemeyer |
| 5,576,351 A | 11/1996 | Yoshimura |
| 5,631,031 A | 5/1997 | Meade |

(Continued)

FOREIGN PATENT DOCUMENTS

| | | |
|---|---|---|
| CN | 1631539 | 6/2005 |
| EP | 1336602 | 8/2003 |

(Continued)

OTHER PUBLICATIONS

CAS Registry No. 89695-59-0 https://chem.nlm.nih.gov/chemidplus/m/89695-59-0, 1984.

Elmore et al., "Compilation of free amino acid data for various food raw materials, showing the relative contributions of asparagin, glutamine, aspartic acid and glutamic acid to the free amino acid coposition", Oct. 2002, JIFSAN Acrylamide in Food Workshop, Chicago. (Year 2002).

(Continued)

*Primary Examiner* — Sarah Pihonak
(74) *Attorney, Agent, or Firm* — Booth Udall Fuller, PLC; Pacer K. Udall

(57) ABSTRACT

Methods of producing an amino acid nitrate supplement drink suitable for human consumption are provided. The methods comprise providing a solid nitrate salt of an amino acid and adding an amount of water to the solid nitrate salt of the amino acid to produce the amino acid and nitrate drink, wherein the amount of water is sufficient to dissolve the solid nitrate salt of the amino acid. In particular implementations, the solid nitrate salt of an amino acid is selected from the group consisting of: creatine nitrate, arginine nitrate, leucine nitrate, isoleucine nitrate, valine nitrate, cysteine nitrate, glycine nitrate, agmatine nitrate, beta-alanine nitrate, N-acetyl cysteine nitrate, aspartic acid nitrate, lysine nitrate, histidine nitrate, norvaline nitrate, ornithine nitrate, glutamine nitrate, citrulline nitrate, and betaine nitrate.

24 Claims, No Drawings

(56) References Cited

U.S. PATENT DOCUMENTS

| | | | |
|---|---|---|---|
| 5,679,704 | A | 10/1997 | Schonafinger et al. |
| 5,965,596 | A | 10/1999 | Harris et al. |
| 6,337,349 | B2 | 1/2002 | Scafetta |
| 6,784,209 | B1 | 8/2004 | Gardiner |
| 7,235,237 | B2 | 6/2007 | Loscalzo et al. |
| 7,777,074 | B2 | 8/2010 | Kramer et al. |
| 7,799,782 | B2 | 9/2010 | Munson |
| 8,034,836 | B2 | 10/2011 | Kramer et al. |
| 8,048,921 | B2 | 11/2011 | Kramer et al. |
| 8,178,572 | B2 | 5/2012 | Kramer et al. |
| 8,183,288 | B2 | 5/2012 | Kramer et al. |
| 8,455,531 | B2 | 6/2013 | Kramer et al. |
| 8,466,187 | B2 | 6/2013 | Kramer et al. |
| 8,569,368 | B2 | 10/2013 | Kramer et al. |
| 8,569,369 | B2 | 10/2013 | Kramer et al. |
| 8,952,045 | B1 | 2/2015 | Kramer |
| 8,952,046 | B1 | 2/2015 | Kramer |
| 8,957,100 | B1 | 2/2015 | Kramer |
| 8,957,101 | B1 | 2/2015 | Kramer |
| 2001/0002269 | A1 | 5/2001 | Zhao |
| 2001/0048952 | A1* | 12/2001 | Siskind ............... A23L 33/175 424/725 |
| 2002/0065323 | A1 | 5/2002 | Crooks |
| 2002/0119933 | A1 | 8/2002 | Butler et al. |
| 2003/0091615 | A1 | 5/2003 | Craig |
| 2003/0119888 | A1 | 6/2003 | Allen |
| 2004/0057926 | A1 | 3/2004 | Ochoa |
| 2004/0087518 | A1 | 5/2004 | Verlaan |
| 2004/0097401 | A1 | 5/2004 | Datta |
| 2005/0287210 | A1 | 12/2005 | Ron |
| 2005/0288372 | A1 | 12/2005 | Ron |
| 2005/0288373 | A1 | 12/2005 | Ron |
| 2006/0029668 | A1 | 2/2006 | Ron |
| 2006/0142382 | A1 | 6/2006 | Morimoto et al. |
| 2006/0182815 | A1 | 8/2006 | Gladwin et al. |
| 2006/0198899 | A1 | 9/2006 | Gardiner |
| 2007/0154569 | A1 | 7/2007 | Gladwin et al. |
| 2008/0026075 | A1 | 1/2008 | Kondo |
| 2008/0233186 | A1 | 9/2008 | Romero |
| 2009/0306208 | A1 | 12/2009 | Shimada |
| 2010/0004335 | A1* | 1/2010 | Kagami ................ A61K 8/02 514/563 |
| 2010/0092441 | A1 | 4/2010 | Lundberg et al. |
| 2012/0220643 | A1* | 8/2012 | Kramer ................ A61P 9/08 514/423 |

FOREIGN PATENT DOCUMENTS

| | | | |
|---|---|---|---|
| GB | 2354441 | 3/2001 | |
| WO | 9843499 | 10/1998 | |
| WO | 0195897 | 12/2001 | |
| WO | 2005115175 | 12/2005 | |
| WO | 2006025286 | 3/2006 | |
| WO | 2006124161 | 11/2006 | |
| WO | 2007000985 | 1/2007 | |
| WO | WO-2007066642 A1 * | 6/2007 | ............ A23K 50/50 |
| WO | 2008105730 | 9/2008 | |
| WO | 2008105731 | 9/2008 | |

OTHER PUBLICATIONS

Pariser et al. cutis, 1994, 54(1): 43-44 respectively.
Stephany et al. "The Intake of Nitrate, Nitrite and Volitile N-Nitrosamins and the Occurrence of Volatile N-nitrosamines in human urine and Veal Calves" IARC Scientific Publicaiton, Jan. 1978, vol. 19, pp. 443-460. (Year 1978).
Lewis et al. publication, Pharmacol. Biochem Behav. 2007, 88(1): 114-21.
Thandani, U. "Challenges with Nitrate Therapy and Nitrate Tolerance: Prevalence, Prevention, and Clinical Relevance" Am J Cardiovasc Drugs, 2014, vol. 14, pp. 287-301. (Year 2014).
Kou et al. application No. 200410009958.3, 2005.
Winter et al., Gastroenterology, 2007, 133: 164-174.
Archer's publicaiton, Journal of food protection, 2002, 64(5): 872-5.
Ignarro et al. publication The Journal of Pharmacology and Experimental Therapeutics, 1988, 244(1): 181-189.
Beverly International advertisement in Dec. 1987 edition of Muscle & Fitness.
Mostad, Zeitschrift fur Kristallographie, 1985, (172): 175-182.
Dhas, S.A. Martin Britto et al., Growth and Characterization of a New Organic NLO Material; Glycine Nitrate, ScienceDirect, Optics Communications 278 (2007) 434-438.
Henriksson et al, Acta Physiol, Sep. 1, 2007, 191:1.
Santamaria et al. "A survey of nitrate and oxalate content in fresh vegetables" Journal of the Science of Food and Agriculture, 1999, vol. 79, 1882-1888 (Year: 1999).
Kemmerer et al. publication, J. Nutr., 1949, 38(4): 527-33.
Gao et al., Life Science, 1995, 57: 83-86.
Sen et al. Journal of Association of Official Analytical Chemists, 61(6): 1389-1394, 1978.
Atanasova, Plant Siol Environ, 2008, 54(2):66-71.
Hui or Shi et al., Handbook of Food Science Technology, and Engineering, 2006, vol. 4, Chapert 170, p. 170-1-170-9.
Elkayam et al. "Prevention of nitrate tolerance with concomitant administration of hydralzaine" Can J CArdiol, 1996, vol. 12, suppl C, pp. 17C-21C. (Year 1996).
Curtis, J., Dec. 6, 2017, "Nitrate-Free Bacon: Myth or Reality", https://firsthandfoods.com/author/jennifer/, pp. 1-2 (Year: 2017).
Fanous, S. "Is Sodium Nitrate Bad for You?", May 20, 2015, Healthline, https://www.healthline.com/health/food-nutrition/is-sodium-nitrate-bad-for-you#1, pp. 1-8. (Year: 2015).
Ximenes et al. "Polargraphic detrmination of nitrate in vegetables", Talanta, 2000, vol. 51, pp. 49-56. (Year: 2000).
Bailey et al. "Dietary nitrate supplementation reduces the O2 cost of low-intensity exercise and enhances tolerance to high-intensity exercise in humans", J. Appl. Physiol., 2009, vol. 107, pp. 1144-1155. (Year 2009).
Gibson et al. "Protective role of the epithelium of the small intestine and colon", Inflamm. Bowel Dis., 1996, vol. 2, No. 4, pp. 279-302, abstract provided. (Year 1996).
Examine.com, "L-Carnitine", Sep. 12, 2014, https://examine.com/supplements/l-carnitine/. (Year:2014).
Fraser et al. publication, circulation, 1983, 67(2): 405-412.
Larsen et al., Acta Physiol, Sep. 1, 2007, 1991: 59-66.
Larsen et al., New England Journal of Medicine, 2006, 2792-2793.
Walker et al., Food additive and Contaminants, 1990, 7(6):717-768.
Pischel et al. CAS: 134:71896, 2001.
Schaefer et al. publication, Intl. J. of Sports Medicine, 2002, 23(6):403-407.
Eto et al. publicaiton, Archives of Physiology and Biochemistry, 1995, 103(2):160-4.
Swensen et al. publication, Intl. J. of Sports medicine, 1994, 15(7):430-4.
Vandenberghe et al. publication, J. Appl physiol, 1997, 83:2055-2063.
Flaherty's, 1989, Drugs, 37:523-550.
Feelisch et al., Eur J. Pharmacol., 1987, 139(1):19-30.
Arenas et al., Muscle & Nerve, 1991, 14:589-604.
Tao, Guo-Hong et al., new Generation Ionic Liquids: Cations Derived From Amino Acids, The Royal Society of Chemistry, ChemComm, 2005-06-09, 3562-3564.
Bauer et al., "Vascular and Hemodynamic Differences Between Organic Nitrates and Nitrites," Journal of Pharmacology and Experimental Therapeutics 280:326-331 (1997).
Niu et al., "Vasorelaxant effect of taurine is diminished by tetraethylammonium in rat isolated arteries," European Journal of Pharmacology 580:169-174 (2008).
Tan et al., "Taurine protects against low-density lipoprotein-induced endothelial dysfunction by the DDAH/ADMA pathway," Vascular Pharmacology 46:338-345 (2007).
Ahtee et al, "Taurine Biological Actions and Clinical Perspectives," J. Nutr. 116:2555-2556 (1986).
Bloomer et al., "Glycine propionyl-L-carnitine increases plasma nitrate/nitrite in resistance trained men," Journal of the International Society of Sports Nutrition 4(22):1-6 (2007).

(56) References Cited

OTHER PUBLICATIONS

Material Safety Data Sheet—Taurine, 2009.
Ramaswamy et al., "Vibrational spectroscopic studies of L-argininium dinitrate," J. Raman Spectrosc. 34:50-56 (2003).
Rajkumar et al., "Infrared and Raman spectra of L-valine nitrate and L-leucine nitrate," J. Raman Spectrosc. 31:1107-1112 (2000).
Petrosyan et al., "L-Histidine nitrates," Journal of Molecular Structure 794:160-167 (2006).
Cromwell et al., "The Biosynthesis and Metabolism of Betaines in Plants," Biochem J. 55:189-192 (1953).
Basheva et al., "Role of Betaine as Foam Booster in the Presence of Silicone Oil drops," Langmuir 16:1000-1013 (2000).
Danov et al., "Mixed Solutions of Anionic and Zwitterionic Surfactant (Betaine): Surface Tension Isotherms, Adsorption, and Relaxation Kinetics," Langmuir 20:5445-5453 (2004).
Sridhar et al, "L-Aspartic Acid Nitrate-L-Aspartic Acid," Acta Cryst. E58:1372-1374 (2002).
Sridhar et al., "Bis (beta-alanine) hydrogen nitrate," Acta Cryst. E57:1004-1006 (2001).
Rao et al., "Structure and Conformational Aspects of the Nitrates of Amino Acids and PNitrate, eptides I. Crystal Structure of Glycylglycine Nitrate," Acta Cryst. B29:2379-2388 (1973).
Bauer et al., Photochemical Generation of Nitric Oxide from Nitro-containing Compounds: Possible Relation to Vascular Photorelaxation Phenomena, Life Science 54(1):PL1-PL4 (1994).
Magg et al., "Nitrogenous Compounds in Sugarbeet Juices," Journal of the American Society of Sugar Beet Technologists 17(2): 154-164 (1972).
Mostad et al., "Crystal and molecular structure of DL-methionine nitrate," CAS 104:197543 (1986).
Pradhan et al., "Effect of Anions on the Solubility of Zwitterionic Amino Acids," J. Chem. Eng. Data 45(1): 140-143.
Terzyan et al., "L-Arginine Nitrates," Journal of Molecular Structure 687:111-117 (2004).
Stryer, Lubert, Biochemistry, Third Edition, W.H. Freeman and Co.: New York, 1988, pp. 16-23, 500-502, and 934-936.
Sastre et al., "Metabolism of agmatine in macrophages: modulation by lipopolysaccharide and inhibitory cytokines," Biochem. J. 330:1405-1409 (1998).
Ishii et al., "High glucose augments arginase activity and nitric oxide production in the renal cortex," Metabolism 53(7):868-874 (2004).
Barger, G. (1914) The Simpler Natural Bases. In R.H.A. Plimmer & F.G. Hopkins (eds.) Monographs on Biochemistry (pp. 157-163) Longmans, Green & Co., London.
Berge et al., "Pharmaceutical Salts," Journal of Pharmaceutical Sciences 66(1):1-18 (1977).
Schwedhelm et al., "Pharmacokinetic and Pharmacodynamics properties of oral L-citrulline and L-arginine: impact on nitric oxide metabolism," BR J Clin Pharmacol 65(1):51-59 (2007).
Jablecka et al., "The influence of two different doses of L-arginine oral supplementation on nitric oxide (NO) concentration and total antioxidant status (TAS) in atherosclerotic patients," Med Sci Monit 10(1):CR29-32 (2004).
Maynard et al., "High Levels of Dietary Carnosine Are Associated with Increased Concentrations of Carnosine and Histidine in Rat Soleus Muscle," J. Nutr. 131:287-290 (2001).
Ruel et al., "Modulation in Angiogenic Therapy Randomized Controlled Trial," J Thorac Cardiovasc Surg 135:762-770 (2008).
Rytlewski et al., "Effects of oral L-arginine on the pulsatility indices of umbilical artery and middle cerebral artery in preterm labor," European Journal of Obstetrics &Gynecology and Reproductive Biology 138:23-28 (2008).
Ignarro ("After 130 years, the molecular mechanism of action of nitroglycerin is revealed," [online], Jun. 11, 2002 [retrieved on May 8, 2016]. Retrieved from the Internet: <http://www.pnas.org/cgi/content/full/99/12/7816?ck=nck>).
Smith et al., "Nitric oxide precursors and congenital heart surgery: A randomized controlled trial of oral citrulline," J. Thorac Cardioasc Surg 132:52-65 (2006).
Rytlewski et al., Effects of prolonged oral supplementation with L-arginine on blood pressure and nitric oxide synthesis in preeclampsia, Eur J Clin Lnvest 35(1):32-37 (2005).
Ming et al., "Thrombin Stimulates Human Endothelial Arginase Enzymatic Activity via RhoA/ROCK Pathway," Circulation 110:3708-3714 (2004).
Romero et al., "Therapeutic Use of Citrulline in Cardiovascular Disease," Cardiovascular Drug Reviews 24(3-4):275-290 (2006).
Oka et al., "A pilot study of L-arginine supplementation on functional capacity in peripheral arterial disease," Vascular Medicine 10:265-274 (2005).
Hayashi et al., "L-citrulline and L-arginine supplementation retards the progression of high-cholesterol-diet-induced atherosclerosis in rabbits," PNAS 102(38): 13681-13686 (2005).
Grasemann et al., "Oral L-arginine supplementation in cystic fibrosis patients: a placebo-controlled study." Eur Respir J 25:62-68 (2005).
Boger, "The Pharmacodynamics of L-Arginine," J. Nutr. 137: 1650S-1655S (2007).
Beghetti et al. "Nitric oxide precursors and congenital cardiac surgery: A randomized controlled trial of oral citrulline. Definition of pulmonary hypertension in Fontan circulation?" J Thorac Cardioasc Surg 132(6): 1501-1502 (2006).
Material Safety Data Sheet—agmatine sulfate salt, 2008.
Material Safety Data Sheet—L-arginine, 2009.
Material Safety Data Sheet—beta-alanine, 2005.
Material Safety Data Sheet—beta-alanine MSDS, 2008.
Material Safety Data Sheet—L-glutamine, 2009.
Material Safety Data Sheet—L-glutamine MSDS, 2008.
Material Safety Data Sheet—L-leucine MSDS, 2008.
Material Safety Data Sheet—L-norvaline, dated unknown.
Material Safety Data Sheet—Urea Ammonium Nitrate Solution, CFIndustries, 2006.
Takahashi et al., "Characterization of the influence of nitric oxide donors on intestinal absorption of macromolecules," International Journal of Pharaceutics 286:89-97 (2004).
Fetih et al., "Nitric oxide donors can enhance the intestinal transport and absorption of insulin and [Asu1,7]-eel Calcitonin in rats," Journal of Controlled Release 106:587-297 (2005).
Fetih et al., "Excellent Absorption Enhancing Characteristics of NO Donors for Improving the Intestinal Absorption of Poorly Absorbable Compound Compared with Conventional Absorption Enhancers," Drug Metab. Pharmacokinet. 21(3):222-229 (2006).
Aniya et al., "Evaluation of Nitric Oxide Formation from Nitrates in Pig Coronary Arteries," Jpn. J. Pharmacol. 71:101-109 (1996).
Luscher, "Endogenous and exogenous nitrates and their role in myocardial ischaemia," Br. J. Clin. Pharmacol. 34:29S-35S (1992).
Shiraki et al., "The Hypotensive Mechanisms of the New Anti-Anginal drug, N-(2-hydroxyethyl)nicotinamide nitrate (SG-75) in Beagle Dogs," Japan J. Pharmacol. 31:921-929 (1981).
Slart et al., "Nitrate Administration Increases Blood Flow in Dysfunctional bu Viable Myocardium, Leading to Improved Assesmetn of Myocardial Viability: A PET Study," J Nucl Med 47:1307-1311 (2006).
Fayers et al., "Nitrate tolerance and the lings with endothelial dysfunction and oxidative stress," Br J Clin pharmacol 56:620-628 (2003).
Knot, "Nitrate Tolerance in Hypertension: New Insight Into a Century-Old Problem," Circ Res 93:799-801 (2003).
Schulz et al., "Functional and Biochecical analysis of Endothelial (Dys)function and NO/cGMP Signaling in Human Blood Vessels with and Without Nitroglycerin Pretreatment," Circulation 105:1170-1175 (2002).
Hatanaka et al., "Stereoselective Pharmacokinetics and Pharmacodynamics of Organic Nitrates in Rats," Journal of Pharmacology and Experimental Therapeutics 298:346-353 (2001).
Dietary Nitrate and Nitrite in Increase Nitric Oxide in Patients with Coronary Artery Disease, Clinical trial available at http://clinicaltrials.gov/ct2/show/NCT00069654.
"Heart attack—Nitrates & vasodilators—Revolution Health," available at http://www.revolutionhealth.com/conditions/heart/herat-attack/medication-types/nitrates-vasodilators/, date unknown.

(56) References Cited

OTHER PUBLICATIONS

"Glyceryl trinitrate—leaflet print—Patient UK," available at http://www.patient.co.uk/printer.asp?dock=30003883, 2008.

"Isosorbide dinitrate—leaflet print—Patient UK," available at http://www.patient.co.uk/printer.asp?doc=30003884, 2009.

"Isosorbide mononitrate—leaflet print—Patient UK," available at http://www.patient.co.uk/printer.asp?dock=30003885, 2008.

"Nitrates and nitrites (PIM G016)," available at http://inchem.org/documents/pims/chemical/img016.htm, downloaded 2011.

Chabot et al., "Characterization of the vasodilator properties of peroxynitrite on rat pulmonary artery: role of poly(adenosine 5'-diphosphoribose synthase," British Journal of Pharmacology 121: 485-490 (1997).

Chang KC et al., NO- and NO2, 1998.

Dessaignes, "Research on Some Products of the Transformation of Creatine," The Chemist—A Monthly Journal, vol. 1, Samual Highley Publishers, London, 1854, pp. 594-597.

Wheatley et al., "Arginine deprivation and tumour cell death arginase and its inhibition," Molecular and Cellular Biochemistry, 244:177-185, 2003.

Harrison, D.G. et al., "The Nitrovasodilators, new Ideas About Old Drugs," Circulation, vol. 87, No. 5, May 1993, pp. 1461-1467).

Stephenson, T., "How children's responses to drugs differe from adults," Br. J. Clin. Pharmacol., 59(6):670-673, 2005.

Stetson, C., "Characteristics of Adults vs. Children." [retrieved on May 4, 2016]. Retrieved from the Internet <URL: http://www.ehow.com/info 8501147 characteristics-adults-vs-children.html>.

An et al., "Composite medical preparation for promoting hair growth," CAS: 143:103285 (2005).

Abd El-Gawad et al., AAPS PharmaSciTech, 2017, 18(5): 1795-1809.

Kenechuwu et al. J. Microencapsul, 2017, 34(6):592-609.

Honikel's publication, Meat Science, 2008, 78: 68-76.

Di Pasquale, mino Acids and Proteins for the Athlete: The Anabolic Edge, 1st Edition, 1997, pp. 99-153.

Zhang et al. publication, Amino acids, 2004, 26:203-207.

Luigi et al., Med. Sci Sports Exerc., 1999, 31(12): 1748-54.

Ekblom et al, The New England Journal of Medicine, 2006, 335; 26, pp. 2792-2793.

\* cited by examiner

AMINO ACID COMPOSITIONS

CROSS REFERENCE TO RELATED APPLICATIONS

This application is a continuation application of the earlier and pending U.S. Utility Patent Application to Ronald Kramer, et. al., titled "Amino Acid Compositions," application Ser. No. 16/746,348, filed Jan. 17, 2020, which is a continuation application of the earlier U.S. Utility Patent Application to Ronald Kramer, et. al., titled "Amino Acid Compositions," application Ser. No. 14/617,571, filed Feb. 9, 2015, now U.S. Pat. No. 10,555,921, which is a continuation application of the earlier U.S. Utility Patent Application to Ronald Kramer, et. al., titled "Amino Acid Compositions," application Ser. No. 13/920,081, filed Jun. 17, 2013, now U.S. Pat. No. 8,952,046, and a continuation application of the earlier and pending U.S. Utility Patent Application to Ronald Kramer, et. al., titled "Amino Acid Compositions," application Ser. No. 14/621,738, filed Feb. 13, 2015, which is a continuation application of the earlier U.S. Utility Patent Application to Ronald Kramer, et. al., titled "Amino Acid Compositions," application Ser. No. 13/920,066, filed Jun. 17, 2013, now U.S. Pat. No. 8,957, 100. U.S. Utility Patent Application to Ronald Kramer, et. al., titled "Amino Acid Compositions," application Ser. No. 13/920,081, filed Jun. 17, 2013, now U.S. Pat. No. 8,952, 046, and U.S. Utility Patent Application to Ronald Kramer, et. al., titled "Amino Acid Compositions," application Ser. No. 13/920,066, filed Jun. 17, 2013 now U.S. Pat. No. 8,957,100, are both continuation applications of the earlier U.S. Utility Patent Application to Ronald Kramer, et. al., titled "Amino Acid Compositions," application Ser. No. 13/038,615, filed Mar. 2, 2011, now U.S. Pat. No. 8,466,187, which is a continuation-in-part application of the earlier U.S. Utility Patent Application to Ronald Kramer, et. al., titled "Amino Acid Compounds," application Ser. No. 12/336, 938, filed Dec. 17, 2008, now U.S. Pat. No. 8,034,836, which is a continuation application of the earlier U.S. Utility Patent Application to Ronald Kramer, et. al., titled "Amino Acid Compounds," application Ser. No. 11/950,273, filed Dec. 4, 2007, now U.S. Pat. No. 7,777,074, which application claims the benefit of the filing date of U.S. Provisional Patent Application 60/973,229 entitled "Amino Acid Compounds" to Ronald Kramer, et. al., filed on Sep. 18, 2007, the disclosures of all of which being hereby incorporated entirely herein by reference.

BACKGROUND

While such amino acids may supplement nutrition, they typically do not provide other benefits, such as increasing vasodilation, increasing oxygen flow to the muscles, enhancing blood circulation, furthering nutrient distribution, boosting human growth hormone (HGH) production, improving physical performance, increasing endurance, speeding recovery from injury and boosting nitric oxide (NO) production, among other uses. For example, these conventional amino acids are typically expensive due to the manner in which they are made, may be slow-acting, may be poorly water-soluble, and may either have no vasodilating properties, or vasodilating properties that manifest only through the administration of undesirably large doses and after lengthy metabolic processes. Therefore, it is desirable to design new amino acid compositions that have properties lacking in conventional amino acids, conventional nitrates, and conventional nitrites alone.

SUMMARY

In one aspect, methods of producing amino acid and nitrate supplement drink suitable for human consumption are disclosed. In one implementation, method comprises providing a solid nitrate salt of an amino acid and adding an amount of water to the solid nitrate salt of the amino acid to produce the amino acid and nitrate drink, wherein the amount of water is sufficient to dissolve the solid nitrate salt of the amino acid. In particular implementations, the solid nitrate salt of an amino acid is selected from the group consisting of: creatine nitrate, arginine nitrate, leucine nitrate, isoleucine nitrate, valine nitrate, cysteine nitrate, glycine nitrate, agmatine nitrate, beta-alanine nitrate, N-acetyl cysteine nitrate, aspartic acid nitrate, lysine nitrate, histidine nitrate, norvaline nitrate, ornithine nitrate, glutamine nitrate, citrulline nitrate, and betaine nitrate.

In some embodiments, the method further comprises providing at least one acceptable additive and combining the at least one acceptable addition with the solid nitrate salt of the amino acid wherein the amount of water is added to the solid nitrate salt of the amino acid and the at least one acceptable to produce the amino acid and nitrate drink. In such embodiments, the amount of water added is an amount sufficient to dissolve the solid nitrate salt of the amino acid and the at least one acceptable additive. In some aspects, the at least one acceptable additive is selected from the group consisting of: a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and a binder.

The foregoing and other aspects, features, and advantages will be apparent to those artisans of ordinary skill in the art from the DESCRIPTION and DRAWINGS, and from the CLAIMS.

DESCRIPTION

Overview, Terminology and Definitions

In describing implementations of the disclosed amino acid compound and related compositions and methods of use, the following terminology will be used in accordance with the definitions and explanations set out below. Notwithstanding, other terminology, definitions, and explanations may be found throughout this document, as well.

As used herein, "composition" is a term used in its broadest sense and may refer to a mixture of constituent substances or ingredients. "Mixture" is a term used in its broadest sense and may refer to two or more constituent substances or ingredients (chemical species present in a system) which have been combined (not necessarily in fixed proportions and not necessarily with chemical bonding and not necessarily so that each substance retains its own chemical identity). Mixtures can be the product of a blending or mixing of chemical substances like elements and compounds, without chemical bonding or other chemical change, so that each ingredient substance retains its own chemical properties and makeup. Mixtures can be either homogeneous or heterogeneous. A homogeneous mixture is a type of mixture in which the composition is uniform. A heterogeneous mixture is a type of mixture in which the composition can easily be identified, as there are two or more phases present. A homogeneous mixture in which there is both a solute and solvent present is also a solution.

As used herein, "compound" is a term used in its broadest sense and may refer to a chemical substance comprising two or more different chemically bonded chemical constituent elements or ingredients, with a fixed ratio or proportion by weight. The atoms within a compound can be held together by a variety of interactions, ranging from covalent bonds to electrostatic forces in ionic bonds. The physical and chemical properties of compounds are different from those of their constituent elements. This is one of the main criteria for distinguishing a compound from a mixture of elements or other substances because a mixture's properties are generally closely related to and dependent on the properties of its constituents. However, some mixtures are so intimately combined that they have some properties similar to compounds. Another criterion for distinguishing a compound from a mixture is that the constituents of a mixture can usually be separated by simple, mechanical means such as filtering, evaporation, or use of a magnetic force, but the components of a compound can only be separated by a chemical reaction. Conversely, mixtures can be created by mechanical means alone, but a compound can only be created (either from elements or from other compounds, or a combination of the two) by a chemical reaction.

Thus, for purposes of this disclosure, the term "composition" may refer to a mixture of at least one amino acid in combination with at least a nitrate, a nitrite, or both from any source.

As used herein, "nitrate" is a term used in its broadest sense and may refer to an nitrate in its many different chemical forms including a salt of nitric acid, a single administration nitrate, its physiologically active salts or esters, its combinations with its various salts, its tautomeric, polymeric and/or isomeric forms, its analog forms, and/or its derivative forms. Nitrate comprises, by way of non-limiting example, many different chemical forms including dinitrate and trinitrate. Nitrates may be salts, or mixed salts, of nitric acid ($HNO_3$) and comprise one nitrogen atom and three oxygen atoms ($NO_3^-$). For the exemplary purposes of this disclosure, nitrate may comprise salts of nitrate such as sodium nitrate, potassium nitrate, barium nitrate, calcium nitrate, and the like. For the exemplary purposes of this disclosure, nitrate may include mixed salts of nitrate such as nitrate orotate, and the like. Furthermore, for the exemplary purposes of this disclosure, nitrates that are commonly used in supplement industry are appropriate sources of nitrates, such as juice, extract, powder and the like of cabbage, spinach, beetroot, artichoke, asparagus, broad bean, eggplant, garlic, onion, green bean, mushroom, pea, pepper, potato, summer squash, sweet potato, tomato, watermelon, broccoli, carrot, cauliflower, cucumber, pumpkin, chicory, dill, turnip, savoy cabbage, celeriac, Chinese cabbage, endive, fennel, kohlrabi, leek, parsley, celery, cress, chervil, lettuce, rocket (also known as rucola or arugula), and the like.

As used herein, "nitrite" is a term used in its broadest sense and may refer to an nitrite in its many different chemical forms including a salt of nitrous acid, a single administration nitrite, its physiologically active salts or esters, its combinations with its various salts, its tautomeric, polymeric and/or isomeric forms, its analog forms, and its derivative forms. Nitrite comprises, by way of non-limiting example, many different chemical forms including dinitrite and trinitrite. Nitrites may be salts, or mixed salts, of nitrous acid ($HNO_2$) and comprise one nitrogen atom and two oxygen atoms ($NO_2^-$). For the exemplary purposes of this disclosure, nitrite may comprise salts of nitrite such as sodium nitrite, potassium nitrite, barium nitrite, calcium nitrite, and the like. For the exemplary purposes of this disclosure, nitrite may comprise mixed salts of nitrite such as nitrite orotate, and the like. Additionally, for the exemplary purposes of this disclosure, nitrite may comprise nitrite esters such as amyl nitrite, and the like. Furthermore, for the exemplary purposes of this disclosure, natural sources of nitrites that are commonly used in supplement industry are appropriate sources of nitrites, such as juice, extract, powder and the like of cabbage, spinach, beetroot, artichoke, asparagus, broad bean, eggplant, garlic, onion, green bean, mushroom, pea, pepper, potato, summer squash, sweet potato, tomato, watermelon, broccoli, carrot, cauliflower, cucumber, pumpkin, chicory, dill, turnip, savoy cabbage, celeriac, Chinese cabbage, endive, fennel, kohlrabi, leek, parsley, celery, cress, chervil, lettuce, rocket (also known as rucola or arugula), and the like.

Nitrates and nitrites are commercially available in various preparations, including natural preparations, and are used in various applications. In the case of ingestion by humans, nitrate ($NO_3^-$) is typically reduced to Nitrite ($NO_2$) in the epithelial cells of blood vessels. In vivo, nitrite ($NO_2^-$) reacts with a thiol donor, principally glutathione, to yield NO.

As used herein, the terms "acceptable additive" or "additive" are used in their broadest sense. Particular implementations of the compositions described in this document may also comprise an additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof), and/or a carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof). These additives may be solids or liquids, and the type of additive may be generally chosen based on the type of administration being used. Those of ordinary skill in the art will be able to readily select suitable pharmaceutically effective additives from the disclosure in this document. In particular implementations, acceptable additives may include, by non-limiting example, calcium phosphate, cellulose, stearic acid, croscarmelose cellulose, magnesium stearate, and silicon dioxide.

As used in this document, the term "effective" is used in its broadest sense, including, by non-limiting example, effective in a clinical trial or effective at causing a physiological change for a specific patient.

As used in this document, the term "acceptable" is used in its broadest sense and may describe ingredients of a composition that meet Food and Drug Administration (FDA) standards, United States Pharmacopeia (USP) standards, US Department of Agriculture (USDA) standards for food-grade materials, commonly accepted standards of the nutritional supplement industry, industry standards, botanical standards, or standards established by any individual. These standards may delineate acceptable ranges of aspects of ingredients of a composition such as edibility, toxicity, pharmacological effect, or any other aspect of a chemical, composition, or preparation used in implementations of a composition.

Amino acids are compounds that containing both a carboxyl group (—COOH) and an amino group (—$NH_2$).

While many biochemically and physiological important amino acids have the basic formula X-R, wherein X is

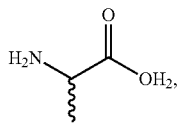

there are biochemically and physiological important amino acids that deviate from the basic formula. Unless specified otherwise, the term "amino acid" as used herein refers to an amino acid in its many different chemical forms, including a single administration amino acid, its physiologically active salts or esters, its combinations with its various salts, its tautomeric, polymeric and/or isomeric forms, its analog forms, its derivative forms, its products of biosynthesis, and/or its decarboxylation products. Accordingly, amino acids comprise, by way of non-limiting example, agmatine, beta alanine, arginine, asparagine, aspartic acid, cysteine, glutamine, glutamic acid, glycine, histidine, L-histidine, leucine, isoleucine, lysine, methionine, phenyl-beta-alanine, proline, serine, threonine, tryptophan, tyrosine, valine, citrulline, creatine, glutamine, norvaline, ornithine, and phenylalanine.

When in the basic form of X-R, amino acids typically differ from one another with respect to the structure of the R group. It is the structure of the R group that typically determines the individuality and character of each amino acid.

For example, the R group for the amino acid arginine is:

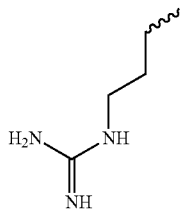

Arginine is characterized as a nonessential amino acid. Specifically, arginine can be independently manufactured by the human body, and does not need to be obtained directly through dietary intake. Arginine plays a significant role in healing, cell division, immune function, the elimination of ammonia from the body and the release of hormones. Arginine is presently used in the dietary supplement industry to supplement Arginine production in the body. Arginine is also presently used in the dietary supplement industry to boost human growth hormone (HGH) production, increase vasodilation, enhance blood circulation, increase oxygen flow to the muscles, and boost nitric oxide (NO) production. Various supplemental arginine forms are available in the consumer marketplace.

The vasodilating effect of ingested arginine takes considerable time to manifest since arginine requires extensive metabolism to yield NO. Additionally, considerable amounts of arginine are required to produce a significant vasodilating effect, with common doses ranging from eight to twenty-four grams per day.

The R group for the amino acid citrulline is:

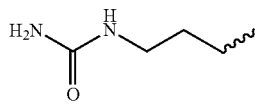

Citrulline is an alpha-amino acid naturally occurring in the human body, and does not need to be obtained directly through dietary intake. In vivo, citrulline is made from the amino acid ornithine, along with carbamoyl phosphate in one of the central reactions in the urea cycle. Citrulline is also produced during the metabolism of Arginine in the body. Citrulline is presently used in the dietary supplement industry to supplement citrulline production in the body. By itself, citrulline has no vasodilating properties. Citrulline is also water insoluble, which reduces its bioavailability and limits the forms in which citrulline may be effectively used.

The amino acid creatine deviates from the basic amino acid formula of X-R as described. The structure of creatine is:

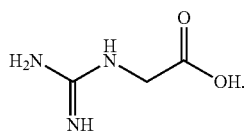

Creatine is a nonessential amino acid and is also a nitrogenous organic acid. Creatine is independently manufactured by the human body, and does not need to be obtained directly through dietary intake. Creatine plays a significant role in providing muscles with energy. Creatine is presently used in the dietary supplement industry to supplement creatine production in the body. Creatine is also presently used in the dietary supplement industry to increase muscle-mass gains, improve athletic performance and strength. Creatine, by itself, has no vasodilating properties. Creatine is also water insoluble, which reduces its bioavailability and limits the forms in which creatine may be effectively used.

The R group for the amino acid glutamine is:

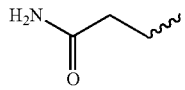

Glutamine is a nonessential amino acid. Glutamine is the most abundant naturally occurring, non-essential amino acid in the human body and is found circulating in the blood, as well as stored in the skeletal muscles. Glutamine plays a significant role in protein synthesis, muscle growth, and wound healing. Glutamine is presently used in the dietary supplement industry to supplement glutamine production in the body. Glutamine is also presently used in the dietary supplement industry to maintain the body's glutamine pool. Glutamine, by itself, has no vasodilating properties. Glutamine is also water insoluble, which reduces its bioavailability and limits the forms in which glutamine may be effectively used. Additionally, glutamine inhibits NO production through downregulation of eNOS synthase.

The R group for the amino acid leucine is:

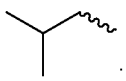

Leucine is an essential amino acid, meaning that leucine is not synthesized in vivo in animals. Accordingly, leucine must be ingested, usually as a component of proteins consumed directly through dietary intake. Leucine plays a significant role in muscle protein synthesis. Leucine can also inhibit protein degradation in skeletal muscle, as well as in the liver. Leucine is presently used in the dietary supplement industry to supplement dietary leucine sources. Leucine is also presently used in the dietary supplement industry to promote anabolism and stimulate muscle protein synthesis. Leucine, by itself, has no vasodilating properties. Leucine is also water insoluble, which reduces its bioavailability and limits the forms in which leucine may be effectively used.

The R group for the amino acid norvaline is:

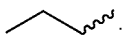

Norvaline is a nonessential amino acid. Specifically, norvaline can be independently manufactured by the human body, and does not need to be obtained directly through dietary intake. Norvaline is presently used in the dietary supplement industry to supplement norvaline production in the body. Norvaline is also presently used in the dietary supplement industry to inhibit the enzyme arginase and thus reduce the conversion of arginine to urea. Norvaline, by itself, has no vasodilating properties, although it enhances the vasodilating properties of arginine. Norvaline is also water insoluble, which reduces its bioavailability and limits the forms in which norvaline may be effectively used.

The R group for the amino acid ornithine is:

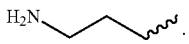

Ornithine is a non-essential amino acid. That is, ornithine is independently manufactured by the human body and does not need to be obtained directly through dietary intake. Ornithine plays a significant role in the synthesis of polyamines, specifically via the action of ornithine decarboxylase. Ornithine is presently used in the dietary supplement industry to supplement dietary ornithine sources. Ornithine is also presently used in the dietary supplement industry to enhance the vasodilating properties in a series of products commonly known as "NO boosters." Ornithine exerts its vasodilating effect only by in vivo conversion to arginine and then by following the pathway that converts arginine to NO. Many grams of ornithine and a considerable amount of time are required in order to assert its vasodilating effect.

The R group for the amino acid histidine is:

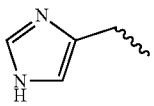

Histidine is a naturally-occurring amino acid and is coded for in DNA. Relatively small shifts in cellular pH will change the electrical charge of histidine. For this reason, histidine finds its way into considerable use as a coordinating ligand in metalloproteins and also as a catalytic site in certain enzymes. Histidine is currently used in the dietary supplement industry to support carnosine production. Histidine, by itself, has no vasodilating properties. Additionally, histidine is very poorly water soluble, a fact that limits its bioavailability and utility. Histidine is presently used in the dietary supplement industry in the forms of single administration histidine and histidine HCl.

The R group for the amino acid beta alanine is:

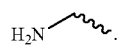

Beta alanine is the only naturally-occurring beta amino acid. A beta amino acid is one in which the amino group is located at the beta position (i.e. two atoms away) from the carboxyl group. Beta alanine is formed in vivo through the degradation of dihydrouracil and carnosine. Beta alanine is the rate-limiting precursor of carnosine. Therefore, carnosine levels are limited by the amount of available beta alanine. Beta alanine, by itself, has no vasodilating properties. Additionally, beta alanine is somewhat water soluble, which limits its bioavailability and utility. Beta alanine is presently used in the dietary supplement industry to support carnosine production.

Agmatine is the decarboxylation product of the amino acid arginine and is an intermediate in polyamine biosynthesis. The structure of agmatine is:

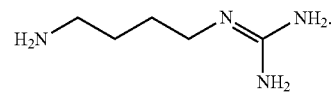

Agmatine is synthesized in the brain and stored in synaptic vesicles in regionally selective neurons. Agmatine is released by depolarization and is inactivated by agmatinase. Agmatine binds to alpha-2-adrenoceptors and imidazoline binding sites. Agmatine likewise blocks N-methyl-D-aspartic acid (NMDA) receptor channels and other ligand-gated cationic channels. Additionally, agmatine inhibits nitric oxide synthase (NOS) and induces the release of some peptide hormones. Agmatine modulates NO through various mechanisms. Agmatine stimulates some types of NOS while inhibiting others. Agmatine inhibits NO production by inhibiting NOS. Agmatine is presently used in the dietary supplement industry in the forms of single administration agmatine and agmatine sulfate.

Carnitine is a quaternary ammonium compound biosynthesized from the amino acids lysine and methionine. Acetyl-L-carnitine is an alternative form of carnitine with an acetyl group coupled with the hydroxyl group of the third carbon molecule. Propionyl-L-carnitine is another alternative form of carnitine that contains a propionyl group coupled with the third carbon molecule. The chemical structure of carnitine is:

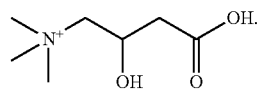

The chemical structure of acetyl-L-carnitine is:

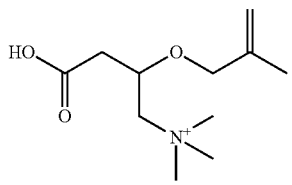

The chemical structure of propionyl-L-carnitine is:

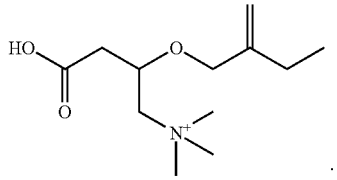 [SMILES: C=C(CC)COC(CC(=O)O)C[N+](C)(C)C]

Significantly, neither carnitine nor its alternative forms possess vasodilating properties. In addition, since carnitine and its alternative forms are bipolar molecules, their solubility might be lowered with respect to pH. Carnitine is presently used in the dietary supplement industry to supplement Carnitine production in the body. Carnitine is also presently used in the dietary supplement industry to improve athletic performance, enhance mood, and boost immune response. Various supplemental Carnitine forms are available in the consumer marketplace.

Taurine is a derivative of the sulfur-containing amino acid cysteine. The structure of taurine is:

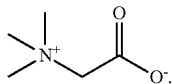

Taurine by itself has no vasodilating properties. Taurine is presently used in the dietary supplement industry to supplement taurine production in the body. Taurine is also presently used in the dietary supplement industry to improve athletic performance and resist muscle cramps. Various supplemental taurine forms are available in the consumer marketplace, including many sports supplements and energy drinks.

Components/Compounds/Compositions

A first implementation is an arginine compound of the formula:

wherein;
R is the arginine group identified and defined above;
X is the amino acid base identified and defined above; and
Y is selected from the group consisting of a nitrate ($NO_3^-$) and a nitrite ($NO_2^-$).

Applicants have cost-effectively synthesized arginine nitrate by combining nitric acid and arginine, mixing with water or another polar, easily evaporated solvent like methanol, alcohol, pyridine, and the like, and leaving to crystallize. Further nitratization can take place, yielding arginine dinitrate or arginine trinitrate. An alternative implementation may comprise using nitrous acid ($HNO_2$) instead of nitric acid ($HNO_3$), thus yielding arginine nitrite. Arginine nitrite has the same effects as arginine nitrate, the only difference being that it requires one less step to yield NO.

A second implementation is a citrulline compound of the formula:

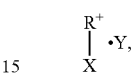

wherein;
R is the citrulline group identified and defined above;
X is the amino acid base identified and defined above; and
Y is selected from the group consisting of a nitrate ($NO_3$) and a nitrite ($NO_2$).

Applicants have cost-effectively synthesized citrulline nitrate by combining nitric acid and Citrulline, mixing with water or another polar, easily evaporated solvent like methanol, alcohol, pyridine, and the like, and leaving to crystallize. Further nitratization can take place, yielding citrulline dinitrate or citrulline trinitrate. An alternative implementation may comprise using nitrous acid ($HNO_2$) instead of nitric acid ($HNO_3$), thus yielding citrulline nitrite. Citrulline nitrite has the same effects as citrulline nitrate, the only difference being that it requires one less step to yield NO. Mixed salts may also be used, such as in the non-limiting example of citrulline nitrate-orotate.

A third implementation is a creatine compound of the formula:

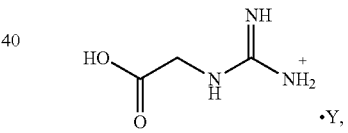

wherein Y is selected from the group consisting of a nitrate ($NO_3^-$) and a nitrite ($NO_2^-$).

Applicants have cost-effectively synthesized creatine nitrate by combining nitric acid and creatine, mixing with water or another polar, easily evaporated solvent like methanol, alcohol, pyridine, and the like, and leaving to crystallize. further nitratization can take place, yielding creatine dinitrate or creatine trinitrate. an alternative implementation may comprise using nitrous acid ($HNO_2$) instead of nitric acid ($HNO_3$), thus yielding creatine nitrite. Creatine nitrite has the same effects as creatine nitrate, the only difference being that it requires one less step to yield NO. Mixed salts may also be used, such as in the non-limiting example of creatine nitrate-orotate.

A fourth implementation is a glutamine compound of the formula:

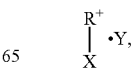

wherein;
R is the gltuamine group identified and defined above;
X is the amino acid base identified and defined above; and
Y is selected from the group consisting of a nitrate ($NO_3^-$) and a nitrite ($NO_2^-$).

Applicants have cost-effectively synthesized glutamine nitrate by combining nitric acid and glutamine, mixing with water or another polar, easily evaporated solvent like methanol, alcohol, pyridine, and the like, and leaving to crystallize. Further nitratization can take place, yielding glutamine dinitrate or glutamine trinitrate. An alternative implementation comprises using nitrous acid ($HNO_2$) instead of nitric acid ($HNO_3$), thus yielding glutamine nitrite. Glutamine nitrite has the same effects as glutamine nitrate, the only difference being that it requires one less step to yield NO. Mixed salts may also be used, such as in the non-limiting example of glutamine nitrate-orotate.

A fifth implementation is a leucine compound of the formula:

wherein;
R is the leucine group identified and defined above;
X is the amino acid base identified and defined above; and
Y is selected from the group consisting of a nitrate ($NO_3^-$) and a nitrite ($NO_2^-$).

Applicants have cost-effectively synthesized leucine nitrate by combining nitric acid and leucine, mixing with water or another polar, easily evaporated solvent like methanol, alcohol, pyridine, and the like, and leaving to crystallize. Further nitratization can take place, yielding leucine dinitrate or leucine trinitrate. An alternative implementation comprises substituting the amino acids valine or isoleucine for leucine. Another alternative implementation comprises substituting nitrous acid ($HNO_2$) for nitric acid ($HNO_3$), thus yielding leucine nitrite. Leucine nitrite has the same effects as leucine nitrate, the only difference being that it requires one less step to yield NO. Mixed salts may also be used, such as in the non-limiting example of leucine nitrate-orotate.

A sixth implementation is a norvaline compound of the formula:

wherein;
R is the norvaline group identified and defined above;
X is the amino acid base identified and defined above; and
Y is selected from the group consisting of a nitrate ($NO_3^-$) and a nitrite ($NO_2^-$).

Applicants have cost-effectively synthesized norvaline nitrate by combining nitric acid and norvaline, mixing with water or another polar, easily evaporated solvent like methanol, alcohol, pyridine, and the like, and leaving to crystallize. Further nitratization can take place, yielding norvaline dinitrate or norvaline trinitrate. An alternative implementation comprises substituting nitrous acid ($HNO_2$) for nitric acid ($HNO_3$), thus yielding norvaline nitrite. Norvaline nitrite has the same effects as norvaline nitrate, the only difference being that it requires one less step to yield NO. Mixed salts may also be used, such as in the non-limiting example of norvaline nitrate-orotate.

A seventh implementation is an ornithine compound of the formula:

wherein;
R is the ornithine group identified and defined above;
X is the amino acid base identified and defined above; and
Y is selected from the group consisting of a nitrate ($NO_3^-$) and a nitrite ($NO_2^-$).

Applicants have cost-effectively synthesized ornithine nitrate by combining nitric acid and ornithine, mixing with water or another polar, easily evaporated solvent like methanol, alcohol, pyridine, and the like, and leaving to crystallize. Further nitratization can take place, yielding ornithine dinitrate or ornithine trinitrate. An alternative implementation comprises using nitrous acid ($HNO_2$) instead of nitric acid ($HNO_3$), thus yielding ornithine nitrite. Ornithine nitrite has the same effects as ornithine nitrate, the only difference being that it requires one less step to yield NO. Mixed salts may also be used, such as in the non-limiting example of ornithine nitrate-orotate.

An eighth implementation is a histidine compound of the formula:

wherein;
R is the histidine group identified and defined above;
X is the amino acid base identified and defined above; and
Y is selected from the group consisting of a nitrate ($NO_3^-$) and a nitrite ($NO_2^-$).

Applicants have cost-effectively synthesized histidine nitrate by combining nitric acid and histidine, mixing with water or another polar, easily evaporated solvent like methanol, alcohol, pyridine, and the like, and leaving to crystallize. Further nitratization can take place, yielding histidine dinitrate or histidine trinitrate. An alternative implementation comprises using nitrous acid ($HNO_2$) instead of nitric acid ($HNO_3$), thus yielding histidine nitrite. Histidine nitrite has the same effects as histidine nitrate, the only difference being that it requires one less step to yield NO. Mixed salts may also be used, such as in the non-limiting example of histidine nitrate-orotate.

A ninth implementation is a beta alanine compound of the formula:

wherein;
R is the beta alanine group identified and defined above;
X is the amino acid base identified and defined above; and
Y is selected from the group consisting of a nitrate ($NO_3^-$) and a nitrite ($NO_2^-$).

Applicants have cost-effectively synthesized beta alanine nitrate by combining nitric acid and beta alanine, mixing with water or another polar, easily evaporated solvent like methanol, alcohol, pyridine, and the like, and leaving to crystallize. Further nitratization can take place, yielding beta alanine dinitrate or beta alanine trinitrate. An alternative implementation comprises using nitrous acid (HNO$_2$) instead of nitric acid (HNO$_3$), thus yielding beta alanine nitrite. Beta alanine nitrite has the same effects as beta alanine nitrate, the only difference being that it requires one less step to yield NO. Mixed salts may also be used, such as in the non-limiting example of beta alanine nitrate-orotate.

A tenth implementation is an Agmatine compound of the formula:

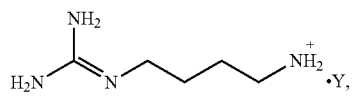

wherein Y is selected from the group consisting of a nitrate (NO$_3^-$) and a nitrite (NO$_2^-$).

Applicants have cost-effectively synthesized agmatine nitrate by combining nitric acid and agmatine, mixing with water or another polar, easily evaporated solvent like methanol, alcohol, pyridine, and the like, and leaving to crystallize. Further nitratization can take place, yielding agmatine dinitrate or agmatine trinitrate. An alternative implementation comprises using nitrous acid (HNO$_2$) instead of nitric acid (HNO$_3$), thus yielding agmatine nitrite. Agmatine nitrite has the same effects as agmatine nitrate, the only difference being that it requires one less step to yield no. Mixed salts may also be used, such as in the non-limiting example of agmatine nitrate-orotate.

Other implementations involve compositions instead of compounds. Using an independent source of nitrates and/or nitrites that is mixed with any of the amino acids disclosed in this document to form a composition can obtain substantially the same effects as the amino acid nitrate or nitrite compounds discussed in this document.

Such an amino acid composition might be depicted by the formula X-R+Y. "X-R" represents an amino acid as discussed previously and "Y" represents a nitrate and/or nitrite. But instead of forming a compound, they are mixed together (represented by the "+") to form a composition.

For the exemplary purposes of this disclosure, following is a variety of specific examples of amino acid compositions.

Composition 1: creatine nitrate 100-1000 mg in capsules. Dosage is 3 capsules twice daily.

Composition 2 (powder form): creatine nitrate 3-3.5 grams+vitamin C 500-1000 mg. Serving size: 4 grams.

Composition 3 (sports drink): arginine nitrate 0.5-3 grams+taurine 0.5-2 grams+1-3 grams sugar or appropriate sweetener+artificial coloring. Mix with purified water to bring volume to 500 ml.

Composition 4 (sublingual tablets; amounts are per tablet): agmatine nitrate 10-100 mg+maltulose 200 mg+artificial cherry flavor. To produce tablets, melt maltulose, slowly add in the agmatine nitrate and the flavoring agent, and pour mixture into the tablet machine.

Composition 5 (tablets containing arginine and potassium nitrate for blood pressure support). Amounts per tablet: arginine 250-700 mg+potassium nitrate 50-500 mg. To produce tablets, add corn starch into the mixture of arginine and potassium nitrate until the desired volume for the tablet machine is obtained.

Composition 6 (airseal capsules for healthy blood pressure support): arginine (as arginine nitrate) 500-1000 mg+celery seed extract 250-500 mg+dried garlic powder 100-300 mg.

Composition 7 (capsules for improved sexual performance): agmatine 500-1000 mg+d-aspartic acid (as d-aspartic acid nitrate) 1-2 grams+dried onion powder (onion also increases testosterone) 1-2 grams.

Composition 8 (improved strength): creatine (as creatine malate) 2-3 grams+calcium nitrate 500 mg.

Composition 9 (improved muscle endurance sports drink): beta alanine 1-2 grams+citrulline (as citrulline nitrate) 250-500 mg+potassium nitrate 100-200 mg+sodium nitrate 50-100 mg+magnesium nitrate 200 mg+artificial coloring+sweetener+flavoring agent. Mix with purified water to bring volume to 500 ml.

Composition 10 (improved muscle anabolism and recovery): leucine 1-5 grams+isoleucine 1-2 grams+valine 1-2 grams+spinach extract (standardized to have a minimum of 1% nitrate content and 10% ecdysterone content minimum) 5 grams.

Composition 11 (timed release tablets for improved mental performance): tyrosine 500-1000 mg+phenylalanine (as phenylalanine nitrate) 250-500 mg+glycine 1000-2000 mg+lithium nitrate 200-300 mg+histidine 300-600 mg.

Composition 12 (growth hormone support): arginine 2-4 grams+ornithine 1-2 grams+magnesium nitrate 500 mg.

Composition 13 (hair growth support as external use cream): lysine nitrite 1 gram+hydroxyproline nitrate 5 grams+methionine nitrate 5 grams+Eucerine® cream base 100 grams.

Composition 14 (immune support effervescent tabs): glutamine 400-800 mg+histidine (as histidine nitrate) 250-500 mg+cysteine (as n-acetyl cysteine) 200-300 mg+parsley powder (standardized for vitamin c and nitrate) 125-250 mg.

Administration and Dosage Forms

Compounds, compositions and/or formulations may be administered in any form, including one of a capsule, a cachet, a pill, a tablet, a powder, a granule, a pellet, a bead, a particle, a troche, a lozenge, a pastille, a solution, an elixir, a syrup, a tincture, a suspension, an emulsion, a mouthwash, a spray, a drop, an ointment, a cream, a gel, a paste, a transdermal patch, a suppository, a pessary, cream, a foam, and combinations thereof for example.

Implementations of amino acid compounds and compositions may conveniently be presented in unit dosage form. Unit dosage formulations may be those containing a daily dose or unit, a daily sub-dose, or an appropriate fraction thereof, of the administered components as described herein.

A dosage unit may include an amino acid compound or composition. In addition, a dosage unit may include an amino acid compound or composition admixed with a pharmaceutically acceptable additive(s), and/or any combination thereof.

The dosage units may be in a form suitable for administration by standard routes. In general, the dosage units may be administered, by non-limiting example, by the topical (including buccal and sublingual), transdermal, oral, rectal, ophthalmic (including intravitreal or intracameral), nasal, vaginal, and/or parenteral (including subcutaneous, intramuscular, intravenous, intradermal, intratracheal, and epidural) routes and many other delivery methods and/or systems known to those of ordinary skill in the art. Implementations of an amino acid compound or composition may also be administered through use of amphipathic lipid delivery systems (such as liposomes and unilamellar vesicles). Those of ordinary skill in the art will readily be able to select additional pharmaceutically acceptable additives to enable delivery of implementations of a pharmaceutical composition from the disclosure in this document.

For the exemplary purposes of this disclosure, oral delivery may be a particularly advantageous delivery route for administration to humans and animals of implementations of a pharmaceutical composition, optionally formulated with appropriate pharmaceutically acceptable additives to facilitate administration.

Manufacture

Implementations of amino acid nitrate and/or nitrite compounds or compositions may be synthesized or created in a wide variety of manners, and may be made from a wide variety of materials. Those of ordinary skill in the art will readily be able to select appropriate materials and methods to manufacture and use the compounds and compositions disclosed herein.

Accordingly, although there are a variety of method implementations for producing pharmaceutical compositions, for the exemplary purposes of this disclosure, a method implementation for producing an amino acid compound may comprise: measuring specific quantities of amino acid, nitric or nitrous acid and water or any other polar, easily evaporated solvent such as methanol, alcohol, pyridine, and the like mixed in a specific order the measured quantities of amino acid, nitric or nitrous acid and water or solvent, and any additional pharmaceutically acceptable additives or inert ingredients, and then separating the pharmaceutical composition into discrete quantities for distribution and/or administration.

Measuring specific quantities of amino acid, nitric or nitrous acid and water or solvent, and pharmaceutically acceptable additives or inert ingredients, may involve any number of steps and implementing components, and measuring specific quantities of amino acid, nitric or nitrous acid and water or solvent, and pharmaceutically acceptable additives or inert ingredients, may be accomplished readily from this disclosure. For the exemplary purposes of this disclosure, measuring specific quantities of amino acid, nitric or nitrous acid and water or solvent, and pharmaceutically acceptable additives or inert ingredients, may comprise using a scale, a solid or liquid dispensing apparatus, or other measurement device capable of measuring solid mass or liquid volume to produce a desired quantity of amino acid, nitric or nitrous acid and water or solvent, and pharmaceutically acceptable ingredient.

It should be appreciated that any of the components of particular implementations of an amino acid compound or composition may be used as supplied commercially, or may be preprocessed by, by non-limiting example, any of the methods and techniques of agglomeration, air suspension chilling, air suspension drying, balling, coacervation, comminution, compression, pelletization, cryopelletization, extrusion, granulation, homogenization, inclusion compoundation, lyophilization, melting, mixed, molding, pan coating, solvent dehydration, sonication, spheronization, spray chilling, spray congealing, spray drying, or other processes known in the art depending in part on the dosage form desired. The various components may also be pre-coated or encapsulated as known in the art. It will also be clear to one of ordinary skill in the art that appropriate additives may also be introduced to the composition or during the processes to facilitate the preparation of the dosage forms, depending on the need of the individual process.

Mixing the measured quantities of amino acid, nitric or nitrous acid and water or solvent, and pharmaceutically acceptable additives or inert ingredients for compounds, or mixing the measured quantities of amino acid, nitrate and/or nitrite sources, and pharmaceutically acceptable additives or inert ingredients for compositions, may involve any number of steps and implementing components, and may be accomplished readily from this disclosure.

For the exemplary purposes of this disclosure, mixing the measured quantities of amino acid, nitric or nitrous acid and water or solvent, and pharmaceutically acceptable additives or inert ingredients, may comprise combining the measured quantities of m amino acid, nitric or nitrous acid and water or solvent, and pharmaceutically acceptable additives or inert ingredients, under the influence of physical, ultrasonic, or electrostatic forces to create a desired degree of intermingling and/or chemical reaction of the amino acid, nitric or nitrous acid and water or solvent and any pharmaceutically acceptable ingredients. The mixed may be accomplished when the amino acid, nitric or nitrous acid and water or solvent and/or any pharmaceutically acceptable ingredients are in a solid, liquid, or semisolid state.

Separating the amino acid compound or composition into discrete quantities for distribution may involve any number of steps and implementing components, and separating the amino acid compound or composition into discrete quantities for distribution may be accomplished readily from this disclosure. For the exemplary purposes of this disclosure, separating the amino acid compound or composition into discrete quantities for distribution may involve utilizing a specific piece of equipment, for example, a conventional tablet forming apparatus to shape the formed composition into individual tablets, each containing a desired dose of amino acid compound or composition. The separating process may be accomplished when the amino acid compound or composition is in a solid, liquid, or semisolid state.

Those of ordinary skill in the art will be able to readily select manufacturing equipment and pharmaceutically acceptable additives or inert ingredients to manufacture implementations of an amino acid compound or composition. For the exemplary purposes of this disclosure, some examples of pharmaceutically acceptable additives or inert ingredients and manufacturing process are included below, particularly those that relate to manufacture of implementations of an amino acid compound or composition in tablet form. Notwithstanding the specific examples given, it will be understood that those of ordinary skill in the art will readily appreciate how to manufacture implementations of an amino acid compound or composition according to the other methods of administration and delivery disclosed in this document.

Accordingly, compounds and compositions may include a acceptable additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or an acceptable carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof).

For example, a particular implementation of an amino acid compound or composition may include a lubricant. Lubricants are any anti-sticking agents, glidants, flow promoters, and the like materials that perform a number of functions in tablet manufacture, for example, such as improving the rate of flow of the tablet granulation, preventing adhesion of the tablet material to the surface of the dies and punches, reducing interparticle friction, and facilitating the ejection of the tablets from the die cavity. Lubricants may comprise, for example, magnesium stearate, calcium stearate, talc, and colloidal silica.

Particular implementations of an amino acid compound or composition may also include a binder. Binders are any agents used to impart cohesive qualities to powdered material through particle-particle bonding. Binders may include, for example, matrix binders (e.g. dry starch or dry sugars), film binders (e.g. celluloses, bentonite, or sucrose), and chemical binders (e.g. polymeric cellulose derivatives, such as methyl cellulose, carboxy methyl cellulose, and hydroxy propyl cellulose), and other sugar, gelatin, non-cellulosic binders, and the like.

Disintegrators may be used in particular implementations of an amino acid compound or composition to facilitate the breakup or disintegration of tablets after administration. Disintegrators may include, for example, starch, starch derivatives, clays (e.g. bentonite), algins, gums (e.g. guar gum), cellulose, cellulose derivatives (e.g. methyl cellulose, carboxymethyl cellulose), croscarmellose sodium, croscarmellose cellulose, and other organic and inorganic materials.

Implementations of an amino acid compound or composition may include diluents, or any inert substances added to increase the bulk of the amino acid compound to make a tablet a practical size for compression. Diluents may include, for example, calcium phosphate, calcium sulfate, lactose, mannitol, magnesium stearate, potassium chloride, and citric acid, among other organic and inorganic materials.

Buffering agents may be included in an amino acid compound or composition and may be any one of an acid and a base, where the acid is, for example, propionic acid, p-toluenesulfonic acid, salicylic acid, stearic acid, succinic acid, tannic acid, tartaric acid, thioglycolic acid, or toluenesulfonic acid, and the base is, for example, ammonium hydroxide, potassium hydroxide, sodium hydroxide, sodium hydrogen carbonate, aluminum hydroxide, calcium carbonate, and other organic and inorganic chemicals.

With respect to delivery of particular implementations of an amino acid compound or composition, for the exemplary purposes of this disclosure, tablets may be utilized. Tablets are any solid pharmaceutical dosage form containing a pharmaceutically acceptable active agent or agents to be administered with or without suitable pharmaceutically acceptable additives and prepared either by compression or molding methods well known in the art. Tablets have been in widespread use and remain popular as a dosage form because of the advantages afforded both to the manufacturer (e.g., simplicity and economy of preparation, stability, and convenience in packaging, shipping, and dispensing) and the patient (e.g., accuracy of dosage, compactness, portability, blandness of taste, and ease of administration). Although tablets are most frequently discoid in shape, they may also be round, oval, oblong, cylindrical, rectangular or triangular, for example. The tablets may be optionally scored so that they may be separated into different dosages. They may differ greatly in size and weight depending on the amount of the pharmaceutically acceptable active agent or agents present and the intended route of administration. They are divided into two general classes: compressed tablets and molded tablets.

Tablets and other orally discrete dosage forms, such as capsules, cachets, pills, granules, pellets, beads, and particles, for example, may optionally be coated with one or more enteric coatings, seal coatings, film coatings, barrier coatings, compress coatings, fast disintegrating coatings, or enzyme degradable coatings for example. Multiple coatings may be applied for desired performance. Further, dosage forms may be designed for, by non-limiting example, immediate release, pulsatile release, controlled release, extended release, delayed release, targeted release, synchronized release, or targeted delayed release. For release/absorption control, carriers may be made of various component types and levels or thicknesses of coats. Such diverse carriers may be blended in a dosage form to achieve a desired performance. In addition, the dosage form release profile may be effected by a polymeric matrix composition, a coated matrix composition, a multi-particulate composition, a coated multi-particulate composition, an ion-exchange resin-based composition, an osmosis-based composition, or a biodegradable polymeric composition.

While manufacture of implementations of an amino acid compound and composition have been described in particular sequences of steps and/or in particular forms, it will be understood that such manufacture is not limited to the specific order of steps or forms as disclosed. Any steps or sequences of steps of manufacture of implementations of an amino acid compound and composition in any form are given as examples of possible steps or sequences of steps or potential forms and not as limitations, since many possible manufacturing processes and sequences of steps may be used to manufacture amino acid compound and composition implementations in a wide variety of forms.

Use

Implementations of an amino acid compound or composition are particularly useful in increasing bioabsorption and vasodilation in humans and animals. However, implementations are not limited to uses relating to bioabsorption or vasodilation modification, and the like. Rather, any description relating to the foregoing is for the exemplary purposes of this disclosure. It will be understood that implementations of an amino acid compound or composition may encompass a variety of uses and are not limited in their uses. For example, possible uses may be, by non-limiting example, prevention of nitrate tolerance, enhanced water solubility, increased distribution to muscles, increased athletic performance, and/or countering NO-inhibiting effects of certain amino acids.

In conventional preparations of nitrate, "tolerance," a particular side effect, has been observed in many patients. This is unfortunate because the effectiveness of nitrate on vasodilation is well documented. "tolerance" occurs when a subject's reaction to nitrate decreases so that larger doses are required to achieve the same effect. A Mar. 3, 2000 report in the *British Journal of Pharmacology* indicates that "tolerance to the dilator effects of nitrates remains a persisting therapeutic problem." Raymond J. MaCallister "Arginine and Nitrate Tolerance" available at http://www.nature.com/bjp/journal/v130/n2/full/0703340a.html, the contents of which are hereby incorporated herein by reference.

Empirical studies indicate that nitrates are useful for their vasolidating effects. Common nitrates include nitroglycerin and isosorbide dinitrate. Nitrates exert their vasodilating effect through their reduction to nitrites. In vivo, nitrates are reduced to nitrites and, in the blood vessels' epithelial cells, nitrite reacts with a thiol donor (mainly glutathione) to yield NO. Louis J. Ignarro, "After 130 Years, the Molecular Mechanism of Action of Nitroglycerin is Revealed" (Jun. 11, 2002) available at http://www.pnas.org/cgi/content/full/99/12/7816?ck=nck, the contents of which are hereby incorporated herein by reference.

The NO-inhibiting characteristics of the amino acid glutamine have been well documented in a number of studies. In particular, a Mar. 28, 2006 report in the *American Journal of Physiology* has found that glutamine inhibits NO production by downregulation of eNOS synthase. Masao Kakoki, et al. "Amino acids as Modulators of Endothelium-Derived Nitric Oxide." available at http://ajprenal.physiology.org/cgi/content/full/291/2/F297, the contents of which are hereby incorporated by reference.

A January 2006 *Journal of Nutrition* report indicates that the Amino Acid Leucine promotes anabolism and stimulates muscle protein synthesis. Michael J. Rennie, et al. "Branched-Chain Amino Acids as Fuels and Anabolic Signals in Human Muscle" available at http://jn.nutrition.org/cgi/content/full/136/1/264S, the contents of which are hereby incorporated by reference.

Empirical studies indicate that the amino acid norvaline inhibits the enzyme arginase and thus decreases the rate of conversion of the amino acid arginine to urea. Takeyori Saheki, et al. "Regulation of Urea Synthesis in Rat Liver" available at http://jb.oxfordjournals.org/cgi/content/abstract/86/3/745?ijkey=5d134456b7443ca36c80926946 2276e532549798&keytype2=tf_ipsecsha, the contents of which are hereby incorporated by reference.

An October 2004 *Journal of Nutrition* report indicates that the amino acid ornithine promotes anabolism and stimulates muscle protein synthesis. Michael J. Rennie, et al. "Branched-Chain Amino Acids as Fuels and Anabolic Signals in Human Muscle" available at http://jn.nutrition.org/cgi/content/full/136/1/264S, the contents of which are hereby incorporated by reference.

Empirical studies indicate that the amino acids beta-beta alanine and L-histidine support carnosine production. M. Dunnett, "Influence of Oral Beta-Beta Alanine and L-Histidine Supplementation on the Carnosine Content of the Gluteus Medius" *Equine Veterinary Journal Supplement*, available at http://www.ncbi.nlm.nih.gov/sites/entrez?Db=pubmed&Cmd=ShowDetailView&TermToSearch=10659307&ordinalpos=4&itool=EntrezSystem2.PEntrez.Pubmed.Pubmed, the contents of which are hereby incorporated by reference.

Empirical studies further indicate that the amino acids beta alanine and L-histidine increase muscle power, recuperation and stamina. Yoshihiro Suzuki "High Level of Skeletal Muscle Carnosine Contributes to the Latter Half of Exercise Performance During 30-S Maximal Cycle Ergometer Sprinting" in the *Japanese Journal of Physiology*, available at http://www.ncbi.nlm.nih.gov/sites/entrez?Db=pubmed&Cmd=ShowDetailView&TermToSearch=12139778&ordinalpos=4&itool=EntrezSystem2.PEntrez.Pubmed.Pubmed_ResultsPanel.Pubmed_RVDocSum, the contents of which are hereby incorporated by reference.

Accordingly, Applicants have discovered that the arginine compound according to the first implementation, when ingested, provides enhanced NO production while providing improved vasodilation effects over single administration of arginine, the single administration of nitrates, or the single administration of nitrites. Improved vasodilation may, in turn, provide better circulation and distribution of arginine in the body. Absorption may be improved since amino acid salts with inorganic acids are much more water soluble than single administration amino acids. Applicants have also discovered that the vasodilating effect of arginine nitrate manifests faster than that of single-administration arginine, and as fast as any nitrate, since the $NO_3^-$ group of the salt requires minimal conversion to yield NO. Additionally a much lesser dose may be required for vasodilation to take place, compared to the single administration of arginine. Likewise, the development of tolerance to the nitrate component of the molecule may be prevented with the presence of arginine. Arginine nitrate may promote vasodilation through production of nitric oxide by two different pathways, the arginine citrullization pathway and the nitrate reduction pathway. Arginine nitrate may likewise be more water soluble than single administration arginine.

Accordingly, Applicants have discovered that the citrulline compound according to the second implementation, when ingested, provides enhanced NO production while providing improved vasodilation effects over single administration of citrulline, the single administration of nitrates, or the single administration of nitrites. Improved vasodilation may, in turn, provide better circulation and distribution of citrulline in the body. Absorption may be improved since amino acid salts with inorganic acids are much more water soluble than single administration amino acids. Additionally a much lesser dose may be required for vasodilation to take place, compared to the single administration of citrulline or nitrates. Citrulline nitrate is likewise more water soluble than single administration citrulline.

Accordingly, Applicants have discovered that the creatine compound according to the third implementation, when ingested, provides enhanced NO production while providing improved vasodilation effects over single administration of creatine, the single administration of nitrates, or the single administration of nitrites. Improved vasodilation may, in turn, provide better circulation and distribution of creatine in the body. Absorption may be improved since amino acid salts with inorganic acids are much more water soluble than single administration amino acids. Additionally a much lesser dose may be required for vasodilation to take place, compared to the single administration of nitrates.

Enhancing a molecule's solubility can enhance its bioavailability, rate of absorption by the GI tract, and as a result, it's concentration in the muscle tissue and its effectiveness. As we have established, the nitrate salts of creatine and other molecules are exceptionally more soluble that their counterparts. Recent studies on creatine nitrate show 1100% improved solubility over creatine monohydrate.

Study 1

Intrinsic Dissolution Profiles of Creatine Nitrate, Creatine Monohydrate and Buffered Creatine Objective: The objective of this study was to determine the dissolution characteristics of three different forms of commercially available creatine including creatine nitrate (CN), creatine monohydrate (CM) and buffered creatine (BC) under different temperature and pH. Methods: Intrinsic dissolution studies were carried out at 37° C. and room temperature in pH 2.5 and 7.4 buffer using modified Wood's apparatus. CN, CM and BC samples (~0.5 g) were compressed in the dies with constant surface area of 1.21 cm$^2$ using a Carver press at 2000 psi with a dwell time of 10 sec. These dies were placed in the USP dissolution apparatus (type II) containing 140 ml of dissolution media, with paddle speed of 50 rpm. Dissolution medium were collected at definite time intervals over a period of 3 hours for CN and 7 hours for both CM and BC and analyzed for creatine using a validated HPLC method. Results: A plot of the amount of creatine dissolved (mg)/surface area (cm2) versus time gives the slope (k') which is directly proportional to the dissolution rate constant. The k' (mg/cm$^2$ hr) values for CN, CM and BC in pH 2.5 buffer at room temperature were 293.0±3.48, 59.1±2.06 and 71.1±0.59. At 37° C. these k' (mg/cm$^2$ hr) values were 327.3±2.66, 97.9±0.88, and 117.9±1.12, respectively. In pH 7.4 buffer, the k' (mg/cm$^2$ hr) values for CN, CM and BC were 278.9±14.6, 52.1±0.22, and 50.6±0.95 at room temperature and 319.5±14.3, 86.0±5.05, and 96.9±9.28 at 37° C., respectively. Conclusions: The dissolution rates of all three creatine forms were higher at 37° C. as compared to at room temperature. CM and BC showed a higher dissolution rate at pH 2.5 than that at pH 7.4, irrespective of temperature. However, the dissolution rate of CN was not affected by the pH of the dissolution media. Comparison of the dissolution profiles for these three creatine forms clearly indicated that CN has the higher intrinsic dissolution rate constant as compared to CM and BC irrespective of temperature and pH of the dissolution media. Results of this study further predict a better bioavailability of CN as compared to CM and BC.

Study 2

Chemical Stability Oof Creatine Nitrate, Creatine Monohydrate and Buffered Creatine in Solution Objective: The objective of this study was to determine the chemical stability of creatine nitrate (CN), creatine monohydrate (CM) and buffered creatine (BC) under two different storage conditions (37° C. in pH 2.5 buffer and 40° C. in pH 6.8 buffer). Methods: A known concentration (~10 mg/ml) of CN, CM and BC were prepared in both pH 2.5 and pH 6.8 buffer and stored in stability chambers in screw capped bottles at 37° C. and 40° C., respectively. Samples were collected at predetermined time points and analyzed for creatine and degradation products if any, using a validated HPLC method. Changes in the pH, clarity and color of the samples were also determined. The order of degradation and rate constant were determined by graphical method. Results: The degradation rate constants (k) for CN, CM and BC at 37° C. in pH 2.5 buffer were 0.075±0.001, 0.119±0.011, and 0.108±0.002 (day$^{-1}$) while that at 40° C. in pH 6.8 buffer were 0.115±0.001, 0.015±0.001, and 0.013±0.002 (day$^{-1}$), respectively. The pH of CN samples at 40° C. in pH 6.8 buffer changed from 2.83±0.01 to 4.31±0.01 within a period of 12 days. The pH changes noticed at 37° C. in pH 2.5 buffer samples over the same period of time for CM, and BC were 3.08±0.01 to 4.12±0.01 and 3.11±0.01 and 4.16±0.01, respectively. No significant change in pH was observed for the rest of the samples. No change in the color and the clarity was noticed over 12 days. Conclusions: All the creatine samples followed first order degradation kinetics under both these experimental conditions. The k value for CN was found to be higher at 40° C. in pH 6.8 buffer as compared to at 37° C. in pH 2.5 buffer. However, both CM and BC showed a faster rate of degradation at 37° C. in pH 2.5 buffer than at 40° C. in pH 6.8 buffer. The major degradation product detected was creatinine. For CN the increase in pH was higher at 40° C. in pH 6.8 buffer as compared to 37° C. in pH 2.5 buffer. However, opposite effect was noticed for both CM and BC.

Study 3

Equilibrium Solubilty Studies of Creatine Nitrate, Creatine Monohydrate and Buffered Creatine Ambrish Pandit, Pinal Mistry, Pat Dib, Alexander Nikolaidis, Alekha K. Dash
Department of Pharmacy Sciences, Creighton University, Omaha, Neb. 68178. Department of Physiological Science UCLA. Aristotle University Of Thessaloniki.

Objective: The objective of this study was to determine the equilibrium solubility of creatine nitrate (CN), creatine monohydrate (CM) and buffered creatine (BC) in water at room temperature as well as in pH 2.5 buffer at room temperature and 37° C. Methods: Excess amount of sample was added to the appropriate solvent and temperature was maintained and agitated at 150 rpm. The supernatant was collected after centrifugation at 24, 48, 72 hours till equilibration and analyzed by a HPLC method. Equilibration was confirmed when the solubility values of two consecutive time points were identical. The pH of the solution was monitored and Differential scanning calorimetry (DSC) thermograms of the solid samples before solubility and of the lyophilized sample after solubility studies were compared. Results: The equilibrium solubility of CN, CM and BC in water at room temperature was reached in 44 hours, and was 210.3±4.82 mg/ml, 19.1±0.40 mg/ml and 19.2±0.55 mg/ml, respectively. However, solubility for CN, CM and BC in pH 2.5 buffer at room temperature was 208.2±6.01 mg/ml, 23.8±0.33 mg/ml, and 21.2±0.09 mg/ml and achieved within 72 hours for CN and in 48 hours for CM and BC samples, respectively. At 37° C. and in pH 2.5 buffer, the equilibrium solubility was reached within 24 hours for all samples and was 325.9±6.10, 31.5±0.71, and 32.6±0.67 for CN, CM, and BC. The pH of solutions of CN, CM and BC in water at room temperature was 0.44±0.04, 8.24±0.14, and 10.03±0.02 respectively. However, these values in pH 2.5 buffer at room temperature were 1.31±0.02, 3.44±0.02 and 3.68±0.01 and at 37° C. this was 1.13±0.07, 3.86±0.47 and 4.42±0.05, respectively. DSC thermograms of the original samples and lyophilized samples were identical. Conclusions: The solubility of creatine nitrate was around 10 fold higher than that of CM or BC under these experimental conditions studied, whereas no significant difference in the solubility of CM and BC were noticed. There was an increase in solubility of each of the creatine forms in pH 2.5 at a higher temperature. DSC analysis confirmed that no phase change was noticed during these solubility studies.

The effectiveness of creatine for increasing athletic performance and improving body composition and muscle anabolism and performance is very well established. Such is also the case for BCAAs (leucine, isoleucine, and valine), taurine and carnitine. It is also well established that for these molecules to have these effects, like all drugs, they must reach the site of action, i.e. the muscle.

Creatine Nitrate & the Athlete

Creatine nitrate excels beyond its superior solubility, stability, and dissolution. That's because creatine nitrate overcomes two primary drawbacks of creatine monohydrate. First, creatine monohydrate results in extreme intra and extracellular water and sodium retention. The intracellular water retention is favorable. Cosmetically speaking however, the extracellular water retention is an unfavorable effect, as an athlete's muscles develop a smooth, soft, and bloated appearance. Second and most importantly, the extreme extracellular water retention may restrict muscle growth. Functionally speaking, the extracellular water retention may push back against muscle cells that are attempting to expand in size.

Creatine nitrate expels excess extracellular water and sodium retention, while simultaneously hydrating and supersaturating muscle cells with creatine. This offers a huge benefit to athletes, encouraging muscle cells to expand in size without resistance from extracellular fluid. In addition, athletes using creatine nitrate may achieve a leaner, drier, and harder look to their muscle tissue; a stark contrast to the puffy and bloated look created by creatine monohydrate. Creatine nitrate however is more than just a salt of creatine, as the nitrate component offers tremendous functional advantages to athletes.

Nitrates provide substantial benefits to athletes and bodybuilders, as supported by clinical research. Nitrates are inorganic anions naturally occurring in the human diet, with close to 80% of dietary nitrates found in vegetables. Fruits and processed meats represent additional sources of nitrates in the human diet. In fact, researchers at Michigan State University have suggested nitrates may be nutritious (13). So what benefit does supplementation with nitrates offer to athletes?

Today, NO and pre-workout nitric oxide performance enhancing formulas have grown in popularity. NO formulas are used to increase muscular "pumps," vasodilation, and nutrient transport to the muscle to assist in greater aerobic performance and recovery. However, most formulas utilize the amino acid L-arginine, a precursor to nitric oxide, as their base. Recently, L-arginine has been proven to be ineffective for elevating NO levels. L-arginine has also been proven ineffective at enhancing athletic performance (9,10, 11). Yet L-arginine is present in nearly every single nitric oxide formula on the market. Contrary to popular belief, most of the "pump" feeling experienced by trainees is derived from an insulin increase following L-arginine supplementation (1).

As recent clinical research confirms, the reduction of inorganic nitrate ($NO_3^-$) and nitrite ($NO_2^-$) in vivo results in NO production. Not only does nitrate generate NO, but nitrate and nitrite are inert end-products of NO oxidation. That is, nitrate converts into NO, and once oxidized, NO is recycled back into nitrate, which then has the potential to convert into NO once again. And the cycle continues to repeat itself. This creates an exciting alternative to nitric oxide production, and carries profound implications for the bodybuilding community.

A critical problem with NO is the short lifespan it has in the body. In just a few seconds, the NO molecule can be metabolized, and the athlete loses any benefit he/she may have received. A pump however must be sustained for several minutes, if not hours, in order to result in those biochemical conditions required to stimulate muscle hypertrophy. And nitrates are capable of elevating NO production for up to 8 hours.

Thus the use of nitrates represents an important alternative to the classical L-arginine-NO-synthase pathway (2) so commonly attempted in various sports supplement formulations.

The efficacy of nitrates in athletic performance is overwhelming in the clinical research. Nitrate consumption significantly enhances NO production, resulting in vasodilation, improved nutrient absorption, increased athletic performance (3), and improved energetic function in working muscles during exercise (12). For example, during low and moderate intensity exercise by humans, supplementation with nitrates has been reported to reduce the amount of oxygen required. During high intensity athletic exercise, nitrate supplementation enhances tolerance to high intensity training, effectively extending the "time to exhaustion"(4).

Organic nitrates also function as permeation enhancers. This is beneficial because enhanced permeation increases intestinal absorption of all nutrients co-ingested. This may allow for a superior quantity of anabolic nutrients to be absorbed and taken up into muscle cells, assisting athletes with the growth and repair of muscle tissue. Nitrates are even able to allow absorption of large macromolecules such as insulin (5,6,7).

For decades, the pharmaceutical industry has used nitrates to induce direct and rapid vasodilation. And today, clinical research is proving that nitrates may produce beneficial effects on blood pressure and cardiovascular health (8). In fact, a recent clinical study investigated the effects of 5 times the amount of nitrates (1,316 mg per day for a 70 kg adult) currently recommended by the World Health Organization (259 mg per day for a 70 kg adult) and showed no adverse health or safety effects. The study results revealed an average reduction in diastolic blood pressure by 4.5 mmHg. Effects on systolic blood pressure were not observed (14, 15).

Nitrates themselves offer many benefits to athletes. Combined with the clinical research behind creatine supporting creatine's positive benefits to athletes, Creatine Nitrate is the first creatine to solve to the solubility, stability, and dissolution challenges while simultaneously providing up to 8 hours of powerful vasodilation that workout enthusiasts demand!

References

The following references are hereby incorporated herein by reference.

1. Glucose—and arginine-induced insulin secretion by human pancreatic B-cells: the role of HERG K+channels in firing and release 2. Does NO metabolism play a role in the effects of vegetables in health?Nitric oxide formation via the reduction of nitrites and nitrates. Dina Ralt*Gertner Institute for Epidemiology and Health Policy Research, Tel Hashomer, Israel 3. Larsen F J, Weitzberg E, Lundberg J O, Ekblom B. Effects of dietary nitrate on oxygen cost during exercise. Acta Physiol (Oxf). 2007 September; 191(1):59-66. Epub 2007 Jul. 17.

4. Stephen J. Bailey,1 Paul Winyard,2 Anni Vanhatalo,1 Jamie R. Blackwell,1 Fred J. DiMenna,1 Daryl P. Wilkerson,1 Joanna Tarr,2 Nigel Benj amin,2 and Andrew M. Jones1. Dietary nitrate supplementation reduces the O2 cost of low-intensity exercise and enhances tolerance to high-intensity exercise in humans. 1School of Sport and Health Sciences and; 2Peninsula College of Medicine and Dentistry, University of Exeter, Exeter, United Kingdom 5. Fetih G, Habib F, Katsumi H, Okada N, Fujita T, Attia M, Yamamoto A. Excellent absorption enhancing characteristics of NO donors for improving the intestinal absorption of poorly absorbable compound compared with conventional absorption enhancers.

6. Koichi Takahashia,* , Nanako Numataa, Natsumi Kinoshitaa, Naoki Utoguchib, Tadanori Mayumic, Nobuyasu Mizunoa. Characterization of the influence of nitric oxide donors on intestinal absorption of macromolecules. International Journal of Pharmaceutics 286 (2004) 89-97

7. Fetih G, Habib F, Okada N, Fujita T, Attia M, Yamamoto A. Nitric oxide donors can enhance the intestinal transport and absorption of insulin and [Asu(1,7)]-eel calcitonin in rats.

8. Supatra Porasuphatanaa, Pei Tsaib, Gerald M. Rosenb. The generation of free radicals by nitric oxide synthase. Comparative Biochemistry and Physiology Part C 134

(2003) 281-289 1532-0456/03/$—see front matter_2002 Elsevier Science Inc. All rights reserved. PII: S1532-045602.00271-5 Review.

9. Olek R A et al. A single oral intake of arginine does not affect performance during repeated Wingate anaerobic test. J Sports Med Phys Fitness. 2010 March; 50(1):52-6.

10. Liu T H, Wu C L, Chiang C W, Lo Y W, Tseng H F, Chang C K. No effect of shortterm arginine supplementation on nitric oxide production, metabolism and performance in intermittent exercise in athletes. J Nutr Biochem. 2008 Aug. 15. [Epub ahead of print]

11. Bescós R, Gonzalez-Haro C, Pujol P, Drobnic F, Alonso E, Santolaria M L, Ruiz O, Esteve M, Galilea P. Effects of dietary L-arginine intake on cardiorespiratory and metabolic adaptation in athletes. Int J Sport Nutr Exerc Metab. 2009 August; 19(4):355-65.

12. Larsen F J, Weitzberg E, Lundberg J O, Ekblom B. Dietary nitrate reduces maximal oxygen consumption while maintaining work performance in maximal exercise. Free Radic Biol Med. 2010 Jan. 15; 48(2):342-7. Epub 2009 Nov. 12.

13. American Journal of Clinical Nutrition, doi:10.3945/ajcn.2008.27131

14. Tanja Sobko, Claude Marcus, Mirco Govoni, Shigeru Kamiya. "Dietary nitrate in Japanese traditional foods lowers diastolic blood pressure in healthy volunteers." Nitric Oxide Volume 22, Issue 2, Pages 136-140

15. http://www.foodnavigator.com/Product-Categories/Preservativesand-acidulants/Dieta ry-nitrates-maybe-beneficial-for-heart-health-Study/?utm_source=Newsletter_Product&utm_medium=email&utm_campaign=Newsletter%2BProduct Accordingly, Applicants have discovered that the glutamine compound according to the fourth implementation, when ingested, counters the NO inhibiting characteristics of glutamine. Absorption of glutamine may be improved since amino acid salts with inorganic acids are much more water soluble than single administration amino acids. Additionally a much lesser dose may be required for vasodilation to take place, compared to the single administration of nitrates. Glutamine nitrate may likewise be more water soluble than single administration glutamine.

Accordingly, Applicants have discovered that the leucine compound according to the fifth implementation, when ingested, provides enhanced NO production while providing improved vasodilation effects over single administration of leucine, the single administration of nitrates, or the single administration of nitrites. Improved vasodilation may, in turn, provide better circulation and distribution of leucine in the body. Absorption may be improved since amino acid salts with inorganic acids are much more water soluble than single administration amino acids. Additionally a much lesser dose may be required for vasodilation to take place, compared to the single administration of nitrates. Leucine nitrate is likewise more water soluble than single administration leucine.

Accordingly, Applicants have discovered that the norvaline compound according to the sixth implementation, when ingested, promotes vasodilation through the inhibition of arginase, while promoting NO formation via the nitrate mechanism. Improved vasodilation may, in turn, provide better circulation and distribution of norvaline in the body. Absorption may be improved since amino acid salts with inorganic acids are much more water soluble than single administration amino acids. Additionally a much lesser dose may be required for vasodilation to take place, compared to the single administration of nitrates. Norvaline nitrate may likewise be more water soluble than single administration norvaline.

Accordingly, Applicants have discovered that the ornithine compound according to the seventh implementation, when ingested, provides an additional vasodilation mechanism, reducing the amount of ornithine needed and the amount of time needed for the vasodilating properties to manifest. Improved vasodilation may, in turn, provide better circulation and distribution of ornithine in the body. Absorption may be improved since amino acid salts with inorganic acids are much more water soluble than single administration amino acids. Applicants have also discovered that ornithine nitrate begins acting as fast as any other nitrate, since the $NO_3$-group of the salt requires minimal conversion to yield NO. Additionally, a much lesser dose may be required for vasodilation to take place, compared to the single administration of nitrates. Ornithine nitrate may likewise be more water soluble than single administration ornithine.

Accordingly, Applicants have discovered that the histidine compound according to the eighth implementation, when ingested, provides a vasodilation mechanism. Vasodilation may, in turn, provide better circulation and distribution of histidine in the body. Applicants have likewise discovered that the histidine compound according to the ninth implementation, when ingested, promotes carnosine production, thus increasing muscle power, endurance and recuperation. Absorption may be improved since amino acid salts with inorganic acids are much more water soluble than single administration amino acids. Applicants have also discovered that histidine nitrate begins acting as fast as any other nitrate, since the $NO_3$-group of the salt requires minimal conversion to yield NO. Additionally, a much lesser dose may be required for vasodilation to take place, compared to the single administration of nitrates. Histidine nitrate may likewise be more water soluble than single administration histidine.

Accordingly, Applicants have discovered that the beta alanine compound according to the ninth implementation, when ingested, provides vasodilation. Vasodilation may, in turn, provide better circulation and distribution of beta alanine in the body. Applicants have likewise discovered that the beta alanine compound according to the tenth implementation, when ingested, promotes carnosine production, thus increasing muscle power, endurance and recuperation. Absorption may be improved since amino acid salts with inorganic acids are much more water soluble than single administration amino acids. Applicants have also discovered that beta alanine nitrate begins acting as fast as any other nitrate, since the $NO_3$-group of the salt requires minimal conversion to yield NO. Additionally, a much lesser dose may be required for vasodilation to take place, compared to the single administration of nitrates. Beta alanine nitrate may likewise be more water soluble than single administration beta alanine.

Accordingly, Applicants have discovered that the agmatine compound according to the eighth implementation, when ingested, counteracts the NO-inhibiting effect of single administration agmatine. Absorption may be improved since amino acid salts with inorganic acids are much more water soluble than single administration amino acids. Applicants have also discovered that agmatine nitrate begins acting as fast as any other nitrate, since the $NO_3$-group of the salt requires minimal conversion to yield NO. Agmatine nitrate may likewise be more water soluble than single administration agmatine.

Accordingly, Applicants have discovered that the carnitine compound, when ingested provides vasodilation. Absorption may be improved since amino acid salts with inorganic acids are much more water soluble than single administration amino acids. Applicants have also discovered that acetyl-1-carnitine nitrate and propionyl-1-carnitine nitrate were able to enhance athletic performance to a greater extent than other salts of carnitine.

Accordingly, Applicants have discovered that not only do the foregoing amino acid nitrate or nitrite compounds provide the effects discussed above, but that amino acid compositions (amino acids mixed with independent sources of nitrates and/or nitrites) enhance bioavailability, absorption, vasodilation, water solubility, distribution to muscles, and the like of certain amino acids, as well as prevent nitrate tolerance and counter nitric oxide inhibiting effects of certain amino acids.

As demonstrated by Anjali Pradhan and Juan Vera, "Effect of Anions on the Solubility of Zwitterionic Amino Acids", *Journal of Chemical and Engineering Data*, Vol 45, 140-143 (2000) (which is hereby incorporated herein by reference), the co-existence of the nitrate ion can enhance the solubility of various amino acids by 300-400%. Although the change in solubility is significantly lower than that of the case of a salt with a nitrate, it is enough to make a difference in absorption in vivo.

Furthermore, the nitrate ion enhances absorption of compounds by the intestine. Nitrates increase bioavailability by: increasing intestinal absorption of nutrients; and increasing vasodilation and blood flow and blood is the carrier of the nutrients to cells. See for example, the following references which are hereby incorporated herein by reference: Takahashi K et al. "Characterization of the influence of nitric oxide donors on intestinal absorption of macromolecules." *Int J Pharm* 2004; 286:89-97; Fetih Get al. "Nitric oxide donors can enhance the intestinal transport and absorption of insulin and [Asu(1,7)]-eel calcitonin in rats." *J Control Release* 2005; 106:287-97; Fetih G et al. "Excellent absorption enhancing characteristics of NO donors for improving the intestinal absorption of poorly absorbable compound compared with conventional absorption enhancers." *Drug Metab Pharmacokinet* 2006; 21:222-9; and Mitchell, G. E., Little, C. O., Jr. & Greathouse, T. R. (1964). "Influence of nitrate and nitrite, on carotene disappearance from the rat intestine." *Life Sci.* 4, 385.

Also, the nitrate ion can cause vasodilatation after reduction to nitrite and then nitric oxide, improve blood circulation, to the muscles and thus distribution of these compounds to the muscle, as well as oxygen distribution to the muscles. Muscle oxygen is needed to provide energy which is needed for all muscle anabolic actions to take place as well as for the active transport of above nutrients via the cell membrane. See the following references which are hereby incorporated herein by reference—Bailey, Stephen G. et al., "Dietary nitrate supplementation reduces the O2 cost of low-intensity exercise and enhances tolerance to high-intensity exercise in humans", *PresS. J Appl Physiol* (Aug. 6, 2009) and Bailey, Stephen G. et al., "Dietary nitrate supplementation enhances muscle contractile efficiency during knee-extensor exercise in humans", *J Appl Physiol* 109:135-148, 2010).

In these same references it is also very well described nitrate's positive effect on athletic endurance and muscle strength. Oxygen is needed by the body to produce energy which by itself is needed for all the metabolic processes in the body, including those that compositions of the present disclosure are involved in. Thus co-administration of nitrate ion with compositions of the present disclosure furthermore increases their distribution to the muscle and their effectiveness.

Therefore, not only does the binding of nitrate salt with compounds improve their bioavailability, absorption and effectiveness, but also the co-administration of nitrate through another nitrate salt, acid or a natural source of nitrate in a composition of the present disclosure shall have similar effects, albeit lower than in the case of nitrate bonded with the molecule.

Via all the above mechanisms, concomitant nitrate or nitrite administration in a composition with an amino acid can substantially increase the concentration of an amino acid in the target muscles (e.g., Neuron cells for the cognitive enhancement properties of phenylalanine, carnitine, glycine, and tyrosine, and muscle cells for the performance enhancing properties of agmatine, arginine, beta alanine, citrulline, creatine, glutamine, L-histidine, isoleucine, leucine, norvaline, ornithine and taurine). In the case of creatine, this is further enhanced by the nitrate's ability to preserve muscle creatine loads.

Therefore, concomitant nitrate or nitrite administration in a composition with an amino acid (just as with amino acid nitrate or nitrite compounds discussed previously) can improve mental focus, cognitive function, athletic and muscle performance, endurance, and strength, and produces much greater synergistic results than the use of only an amino acid alone or a nitrate and a nitrite alone.

What is claimed is:

1. A method of producing amino acid and nitrate supplement drink suitable for human consumption, the method comprising:
   providing a solid nitrate salt of an amino acid; and
   adding an amount of water to the solid nitrate salt of the amino acid to produce the amino acid and nitrate supplement drink.

2. The method of claim 1, wherein the solid nitrate salt of an amino acid is selected from the group consisting of: creatine nitrate, arginine nitrate, leucine nitrate, isoleucine nitrate, valine nitrate, cysteine nitrate, glycine nitrate, agmatine nitrate, beta-alanine nitrate, N-acetyl cysteine nitrate, aspartic acid nitrate, lysine nitrate, histidine nitrate, norvaline nitrate, ornithine nitrate, glutamine nitrate, citrulline nitrate, taurine nitrate, and betaine nitrate.

3. The method of claim 1, wherein the solid nitrate salt of an amino acid is creatine nitrate.

4. The method of claim 1, wherein the solid nitrate salt of an amino acid is arginine nitrate.

5. The method of claim 1, wherein the solid nitrate salt of an amino acid is leucine nitrate.

6. The method of claim 1, wherein the solid nitrate salt of an amino acid is isoleucine nitrate.

7. The method of claim 1, wherein the solid nitrate salt of an amino acid is valine nitrate.

8. The method of claim 1, wherein the solid nitrate salt of an amino acid is cysteine nitrate.

9. The method of claim 1, wherein the solid nitrate salt of an amino acid is glycine nitrate.

10. The method of claim 1, wherein the solid nitrate salt of an amino acid is agmatine nitrate.

11. The method of claim 1, wherein the solid nitrate salt of an amino acid is beta-alanine nitrate.

12. The method of claim 1, wherein the solid nitrate salt of an amino acid is N-acetyl cysteine nitrate.

13. The method of claim 1, wherein the solid nitrate salt of an amino acid is aspartic acid nitrate.

14. The method of claim 1, wherein the solid nitrate salt of an amino acid is lysine nitrate.

15. The method of claim 1, wherein the solid nitrate salt of an amino acid is histidine nitrate.

16. The method of claim 1, wherein the solid nitrate salt of an amino acid is norvaline nitrate.

17. The method of claim 1, wherein the solid nitrate salt of an amino acid is ornithine nitrate.

18. The method of claim 1, wherein the solid nitrate salt of an amino acid is glutamine nitrate.

19. The method of claim 1, wherein the solid nitrate salt of an amino acid is citrulline nitrate.

20. The method of claim 1, wherein the solid nitrate salt of an amino acid is betaine nitrate.

21. The method of claim 1 further comprising:
providing at least one acceptable additive is selected from the group consisting of: a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and a binder; and
combining the at least one acceptable additive with the solid nitrate salt of the amino acid,
wherein the amount of water is added to the solid nitrate salt of the amino acid and the at least one acceptable additive to produce the amino acid and nitrate supplement drink and the amount of water added is an amount sufficient to dissolve the solid nitrate salt of the amino acid and the at least one acceptable additive.

22. The method of claim 21, wherein at least one acceptable additive is selected from the group consisting of: a sweetener, a flavoring agent, and an antioxidant.

23. The method of claim 1, wherein the amount of water is sufficient to dissolve the solid nitrate salt of the amino acid.

24. The method of claim 1, wherein the solid nitrate salt of an amino acid is taurine nitrate.

* * * * *